US009011169B2

(12) United States Patent
Russell et al.

(10) Patent No.: US 9,011,169 B2
(45) Date of Patent: Apr. 21, 2015

(54) CONNECTORS WITH ELECTRICAL OR SIGNAL CARRYING CAPABILITIES AND RELATED METHODS

(71) Applicant: Bal Seal Engineering, Inc., Foothill Ranch, CA (US)

(72) Inventors: Mark Russell, Foothill Ranch, CA (US); Derek Changsrivong, Foothill Ranch, CA (US); Steve Rust, Foothill Ranch, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 0 days.

(21) Appl. No.: 13/848,678

(22) Filed: Mar. 21, 2013

(65) Prior Publication Data
US 2013/0288501 A1    Oct. 31, 2013

Related U.S. Application Data

(60) Provisional application No. 61/613,904, filed on Mar. 21, 2012.

(51) Int. Cl.
| | | |
|---|---|---|
| *H01R 13/52* | (2006.01) | |
| *H01R 13/648* | (2006.01) | |

(Continued)

(52) U.S. Cl.
CPC ......... *H01R 13/648* (2013.01); *Y10T 29/49208* (2015.01); *H01R 43/26* (2013.01); *H01R 13/187* (2013.01); *H01R 13/2421* (2013.01); *H01R 24/58* (2013.01); *A61N 1/3752* (2013.01)

(58) Field of Classification Search
CPC ............. H01R 13/5224; H01R 13/648; H01R 13/5219; H01R 13/5202; H01R 13/521; H01R 13/2421; H01R 13/187

USPC .......................................... 439/271, 827, 521
See application file for complete search history.

(56) References Cited

U.S. PATENT DOCUMENTS 3,171,887 A  *  3/1965  Cross et al. ................... 174/355
5,871,514 A       2/1999  Wiklund et al.
(Continued)

OTHER PUBLICATIONS

International Search Report completed Jul. 24, 2013 from corresponding International Application No. PCT/US2013/033379 filed Mar. 21, 2013 (5 pages).

(Continued)

*Primary Examiner* — Abullah Riyami
*Assistant Examiner* — Vladimir Imas
(74) *Attorney, Agent, or Firm* — Klein, O'Neill & Singh, LLP

(57) ABSTRACT

Aspects of the present disclosure include a connector, an array of connectors, a method for manufacturing the connectors, and a method for using the connectors. The connectors are capable of carrying electrical or electric signal and include geometries to operate in holding, latching, or locking applications. The connector can include a contact housing formed by a first electrically conductive housing, a second electrically conductive housing and a housing sealing component at least partially isolating said first and second electrically conductive housings from each other. A body, such as a pin, a rod, or an elongated member, is provided. A first electrically conductive spring is located in a first groove and a second electrically conductive spring is located in a second groove inside the contact housing. Wherein a first electrical path and a second electrical path are formed when the body is inserted into the contact housing. In other examples, more than two electrical paths can be provided.

40 Claims, 27 Drawing Sheets

(51) Int. Cl.
*H01R 43/26* (2006.01)
*H01R 13/187* (2006.01)
*H01R 13/24* (2006.01)
*H01R 24/58* (2011.01)
*A61N 1/375* (2006.01)

(56) References Cited

U.S. PATENT DOCUMENTS

| | | | |
|---|---|---|---|
| 6,705,898 B2 * | 3/2004 | Pechstein et al. | 439/660 |
| 6,895,276 B2 | 5/2005 | Kast et al. | |
| 7,167,749 B2 * | 1/2007 | Biggs et al. | 607/36 |
| 7,530,842 B1 * | 5/2009 | Hsu | 439/578 |
| 7,581,989 B1 * | 9/2009 | Wheatley | 439/589 |
| 7,837,502 B2 * | 11/2010 | Van Swearingen et al. | 439/578 |
| 7,862,353 B1 * | 1/2011 | Azad et al. | 439/157 |
| 8,057,270 B2 * | 11/2011 | Shimazu et al. | 439/827 |
| 8,167,660 B2 * | 5/2012 | Dilmaghanian et al. | 439/669 |
| 8,378,218 B2 * | 2/2013 | Dicken et al. | 174/126.1 |
| 8,403,679 B2 * | 3/2013 | Berard et al. | 439/24 |
| 8,461,456 B2 * | 6/2013 | Bernauer | 174/152 G |
| 8,491,345 B2 * | 7/2013 | Leon et al. | 439/817 |
| 8,506,314 B2 * | 8/2013 | Gramsamer et al. | 439/289 |
| 8,519,727 B2 * | 8/2013 | Yamamoto | 324/755.05 |
| 2004/0093038 A1 | 5/2004 | Biggs et al. | |
| 2009/0018601 A1 | 1/2009 | Deininger et al. | |
| 2010/0233896 A1 * | 9/2010 | Dilmaghanian | 439/271 |
| 2010/0304622 A1 | 12/2010 | Shimazu et al. | |

OTHER PUBLICATIONS

Written Opinion completed Jul. 24, 2013 from corresponding International Application No. PCT/US2013/033379 filed Mar. 21, 2013 (10 pages).

* cited by examiner

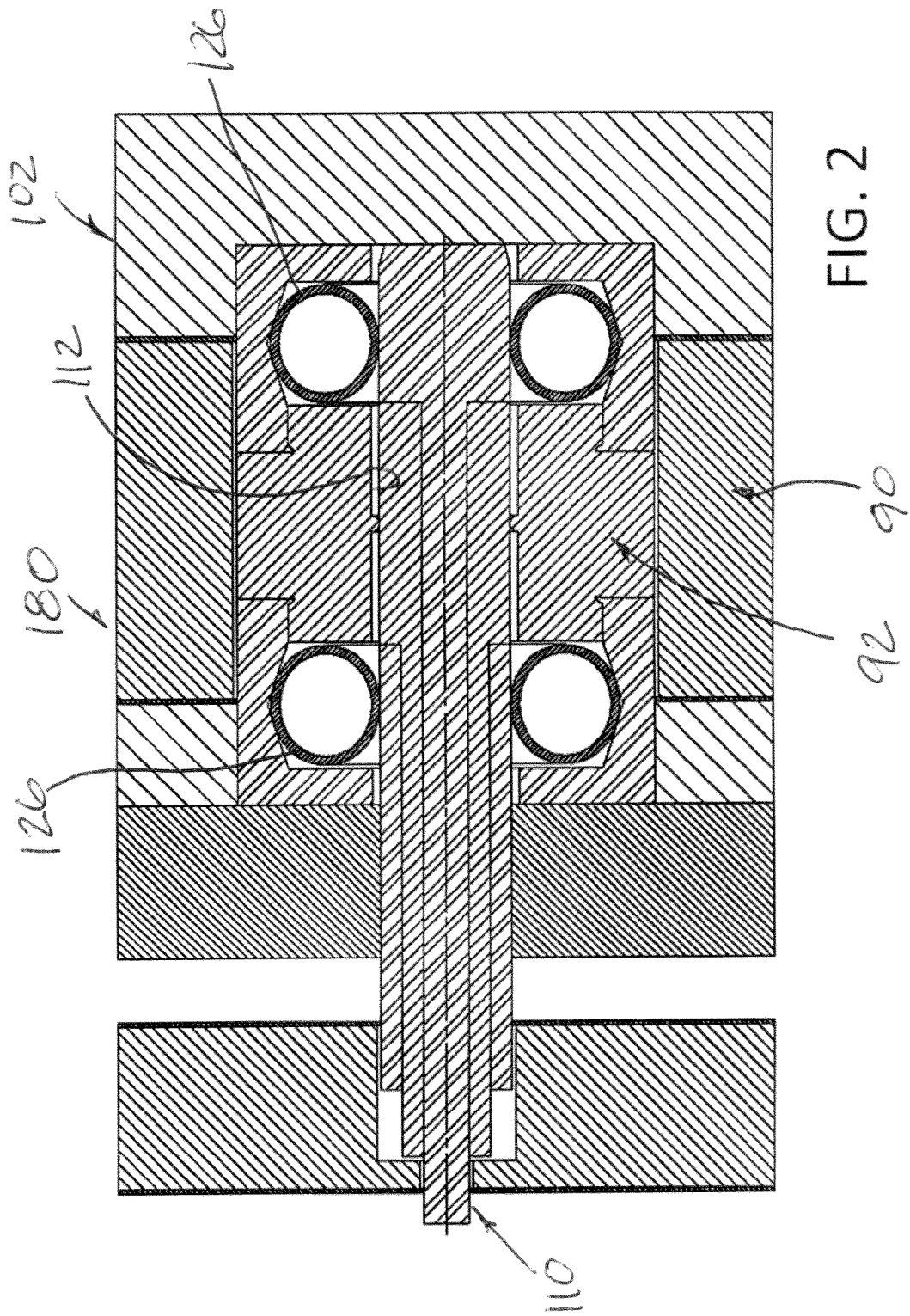

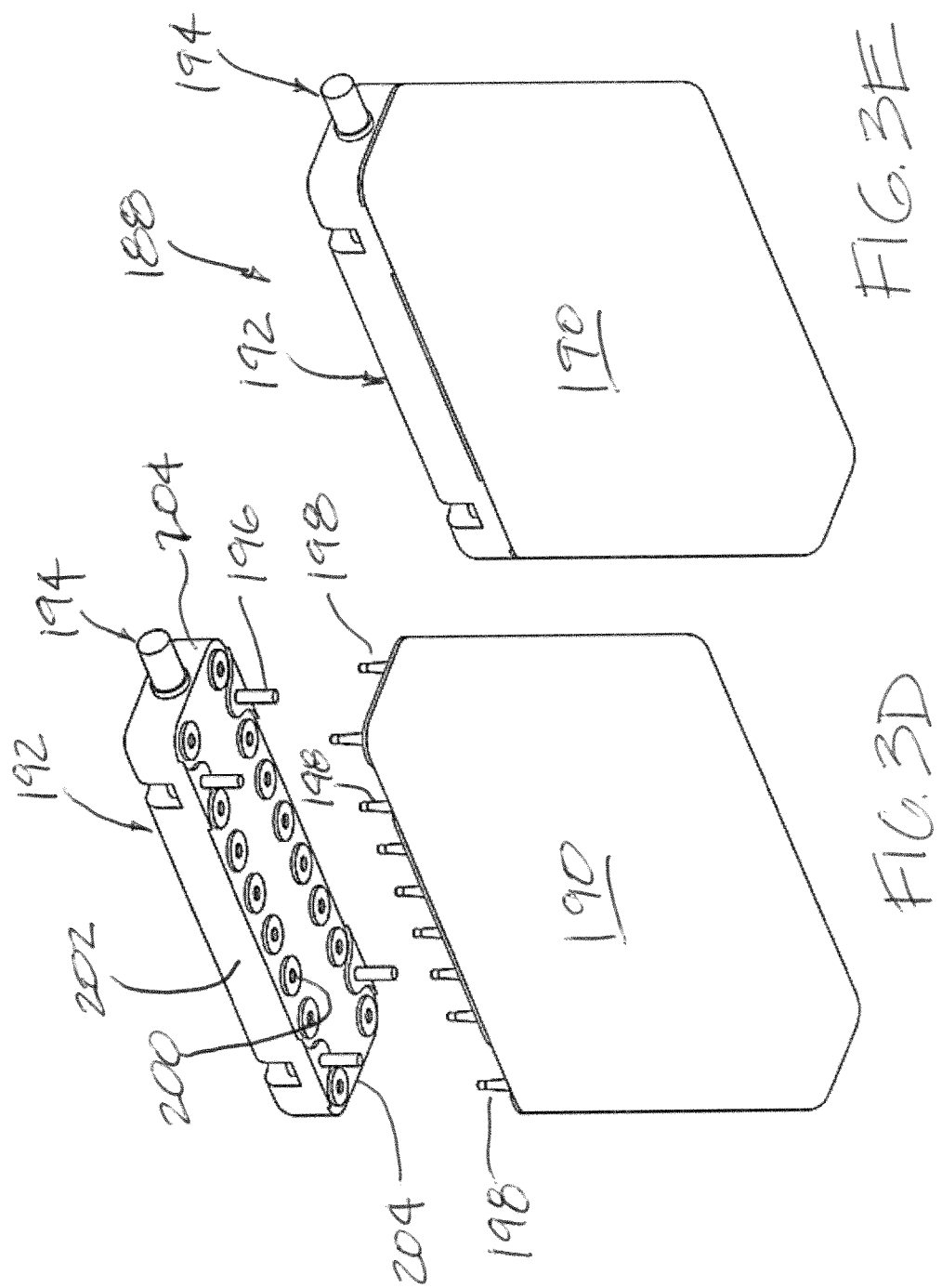

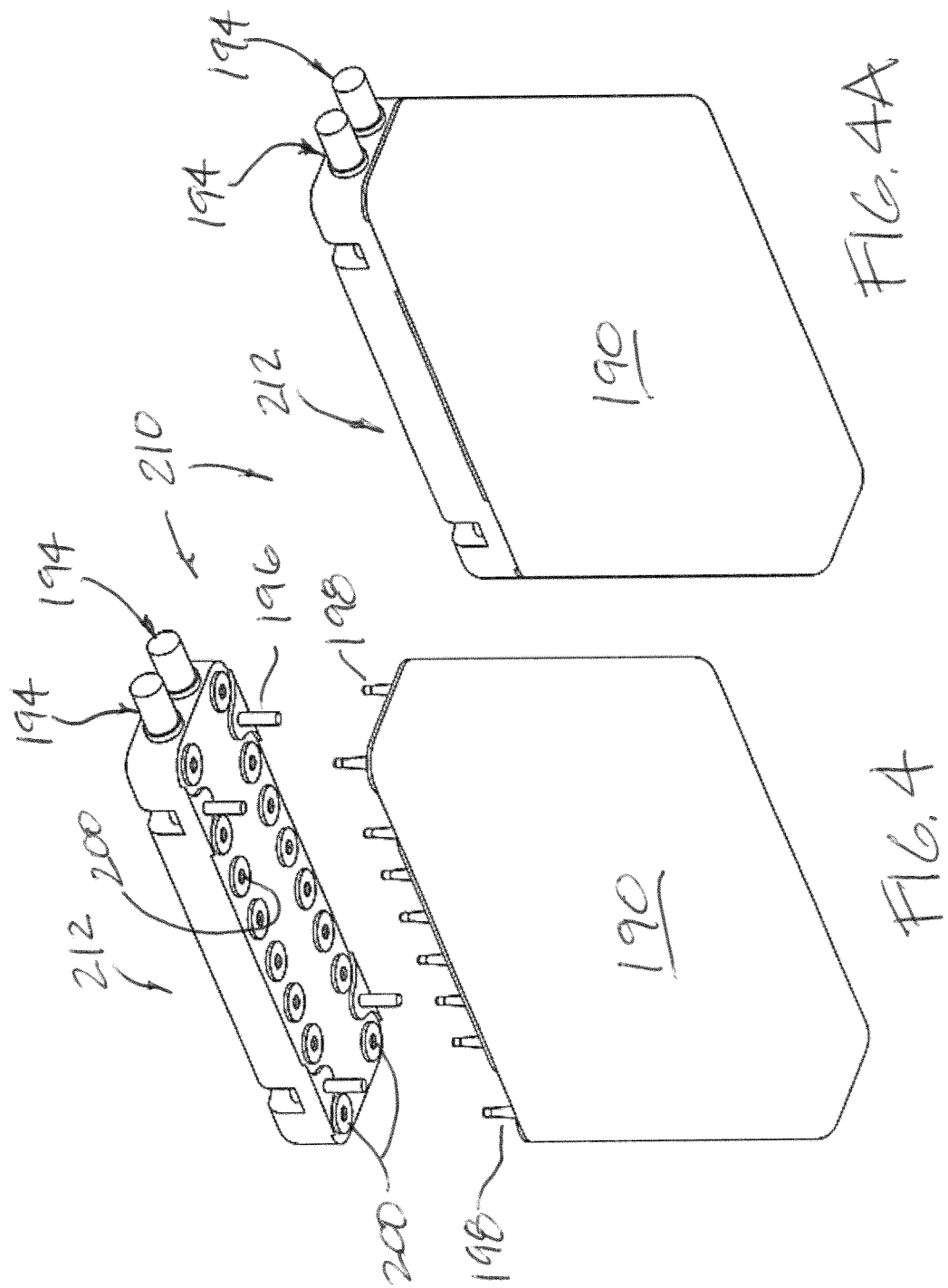

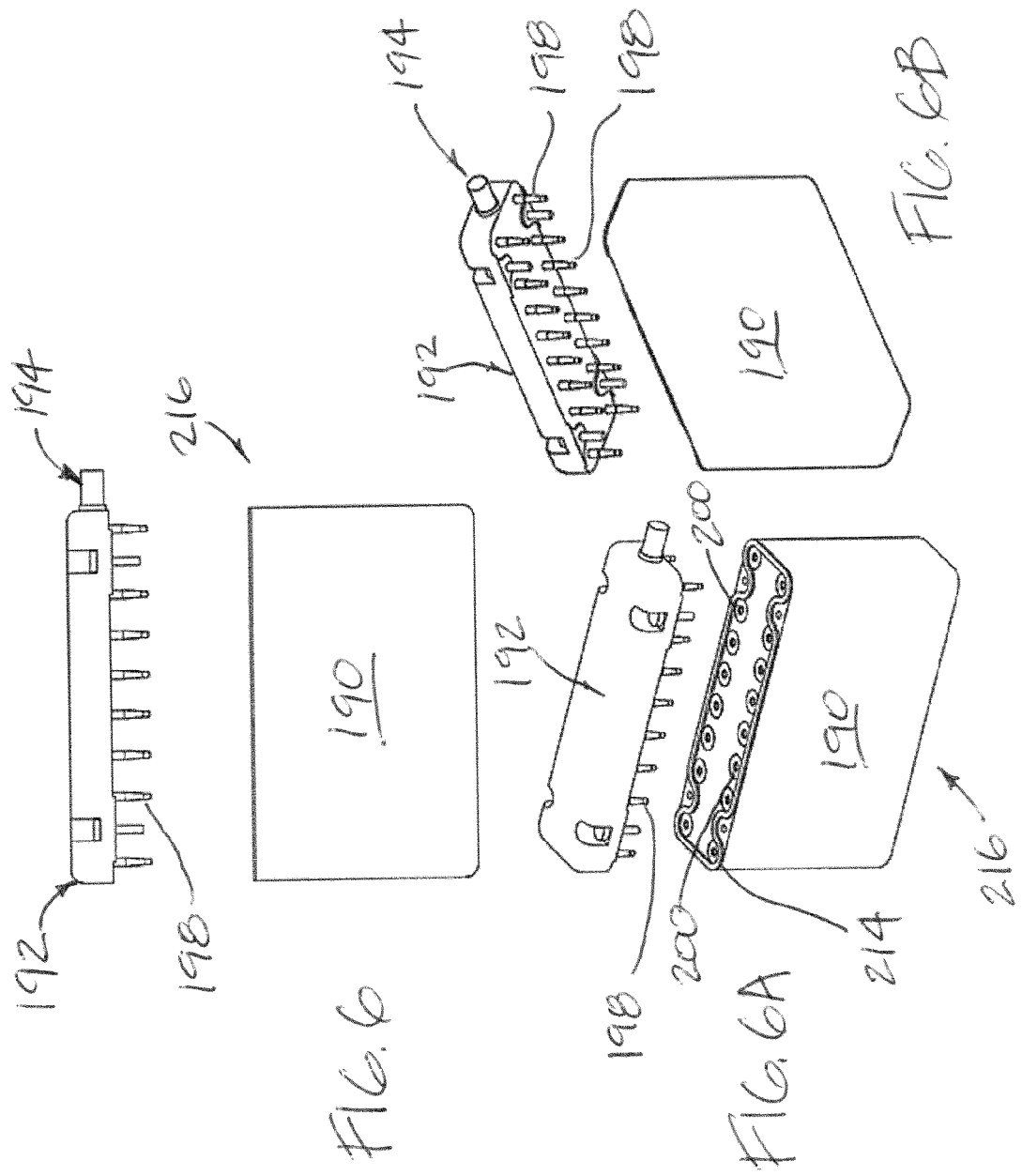

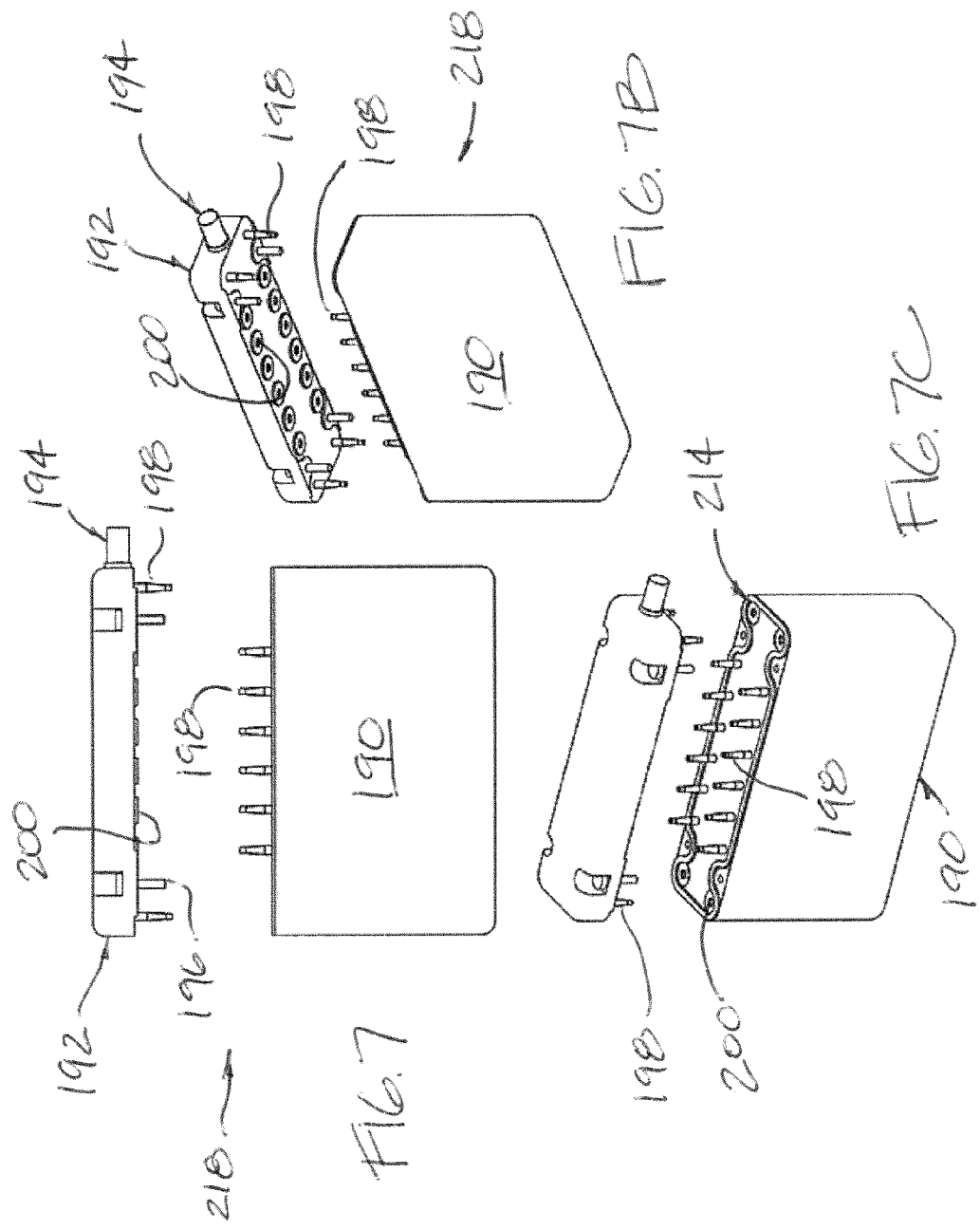

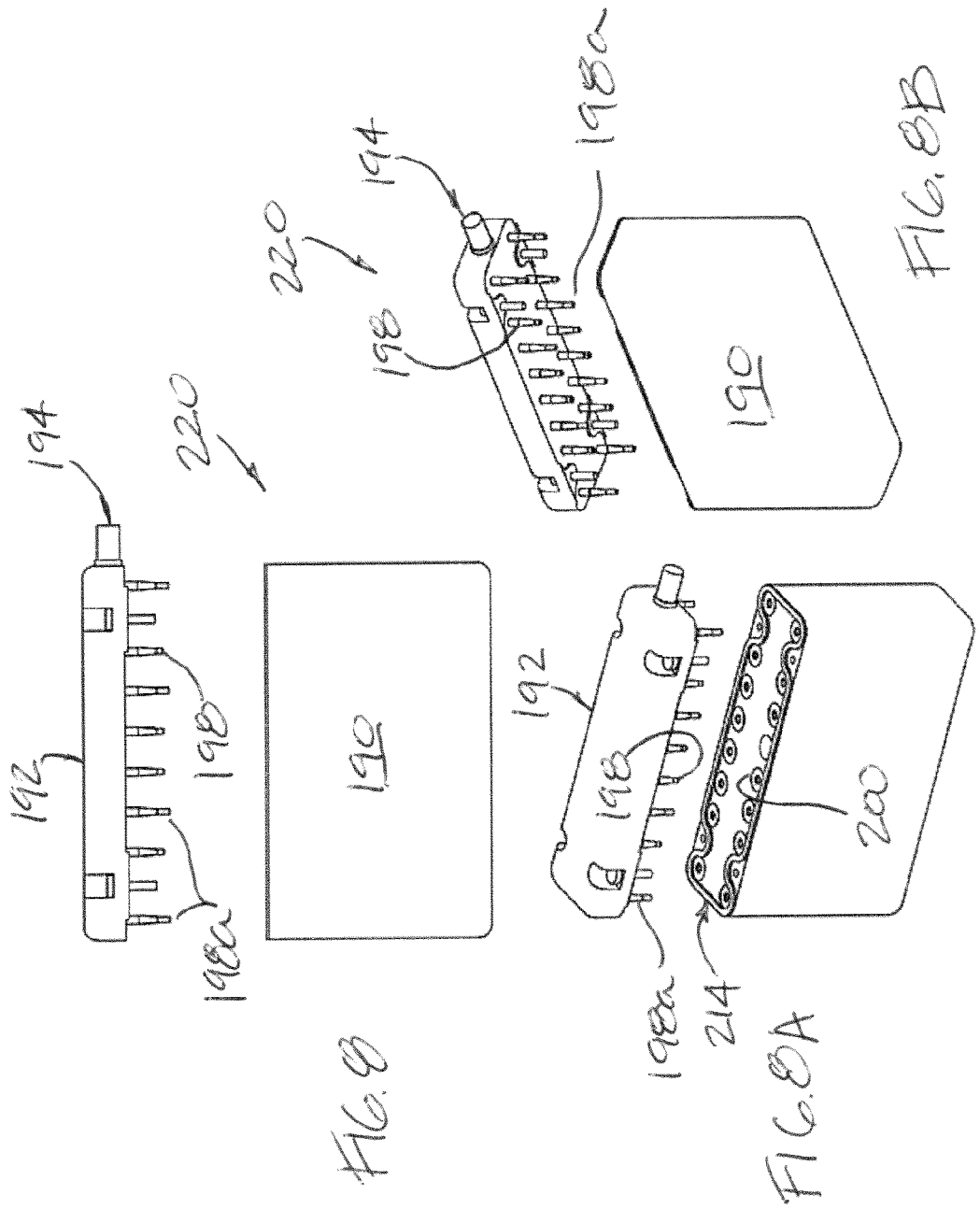

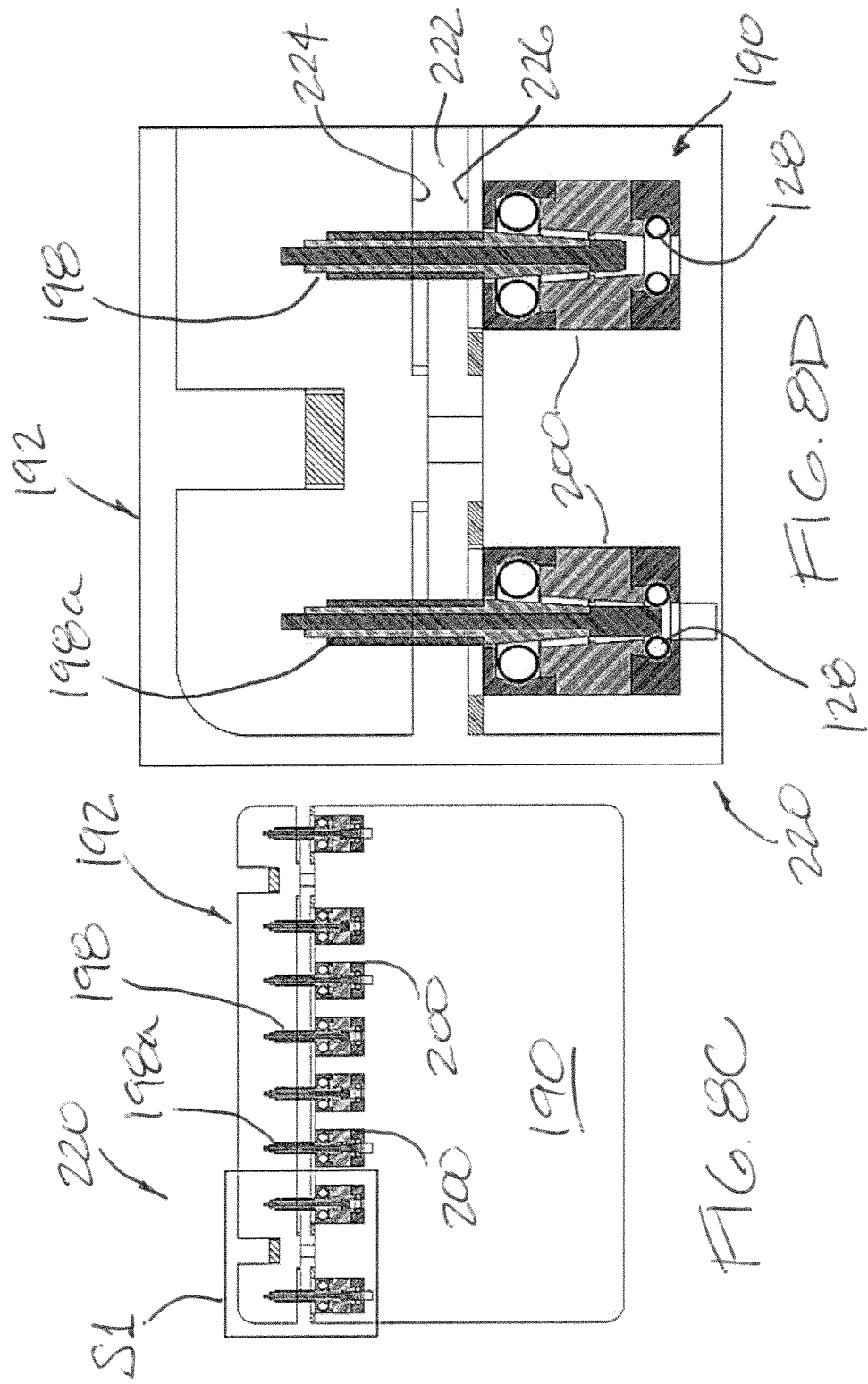

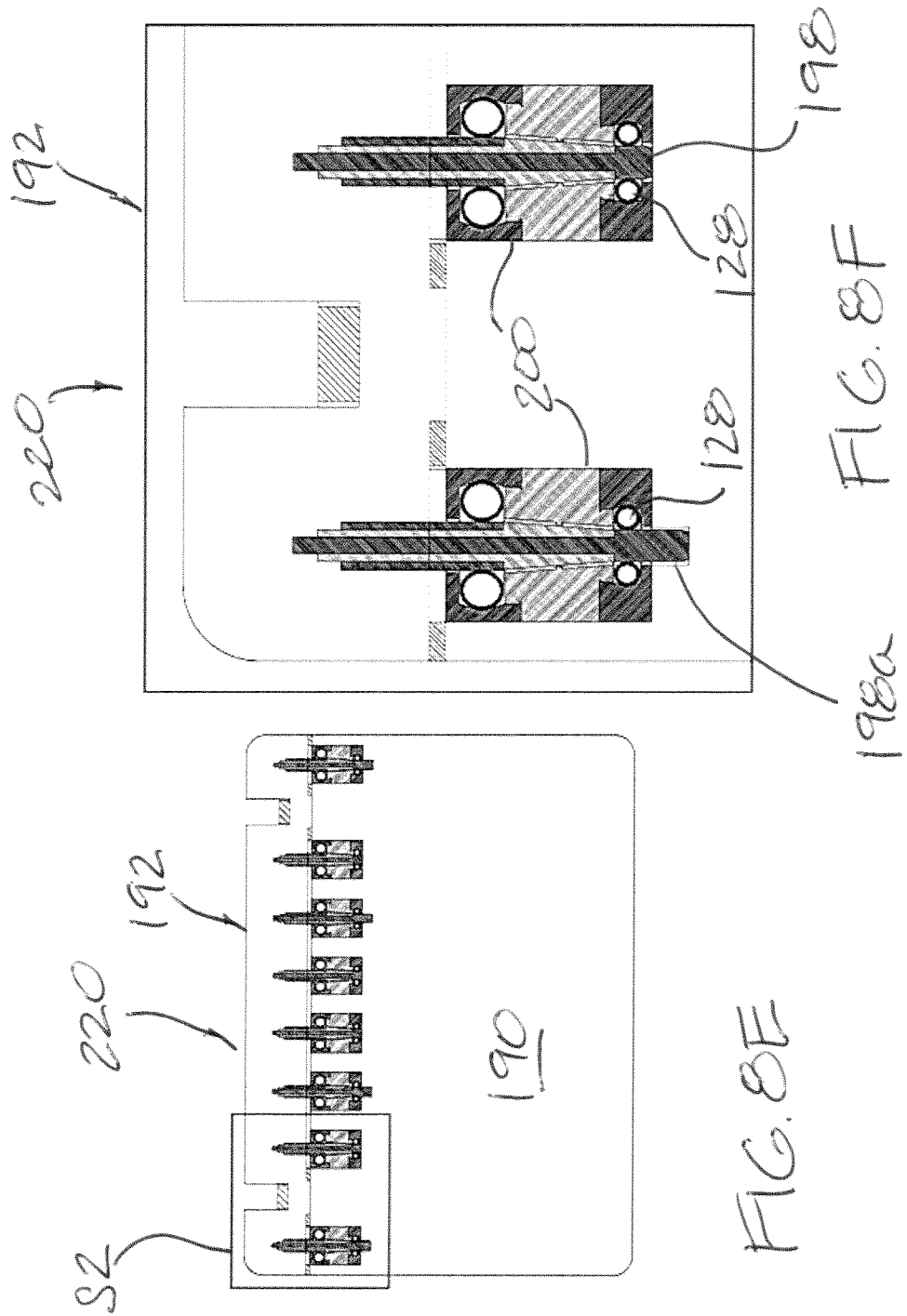

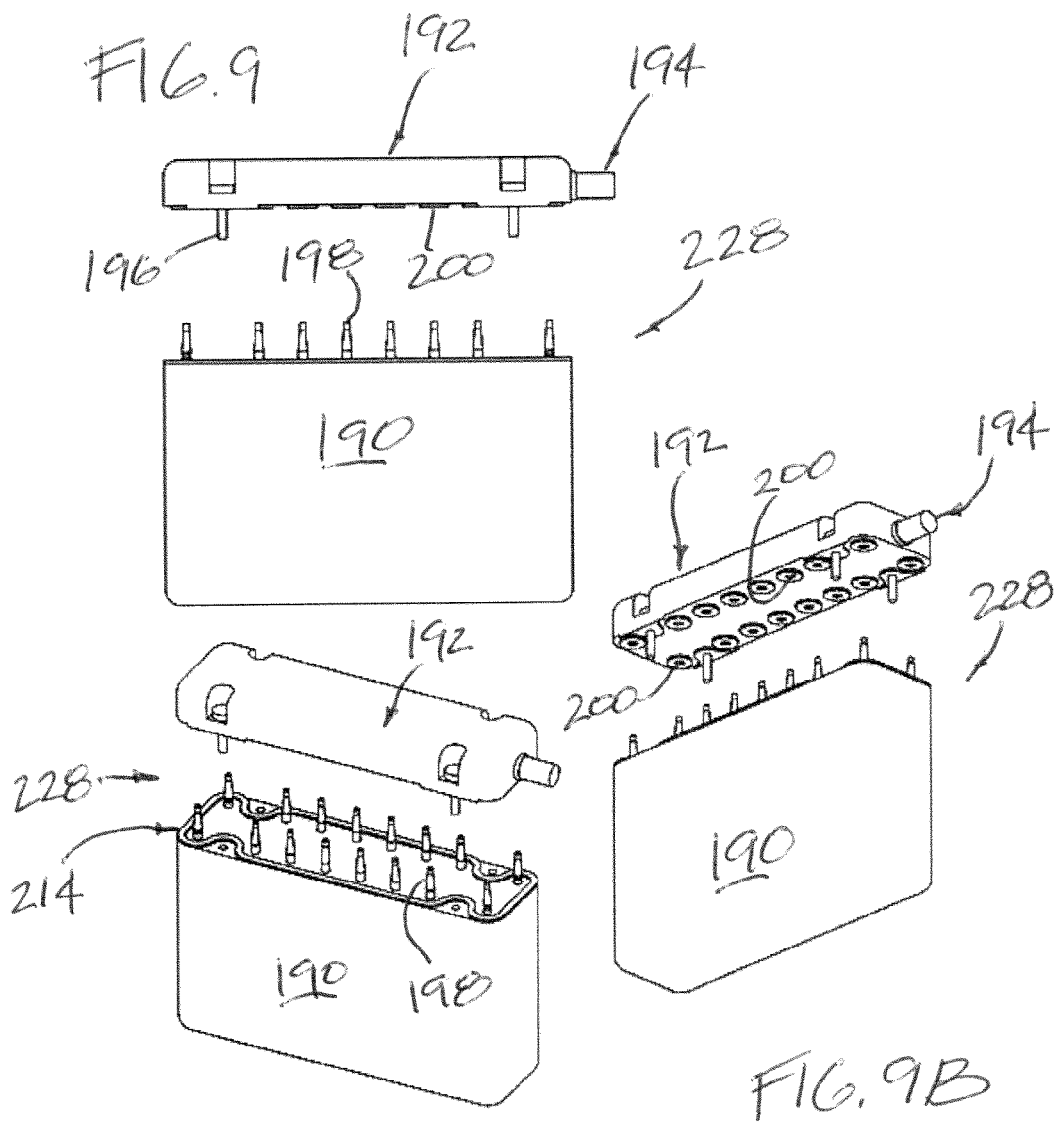

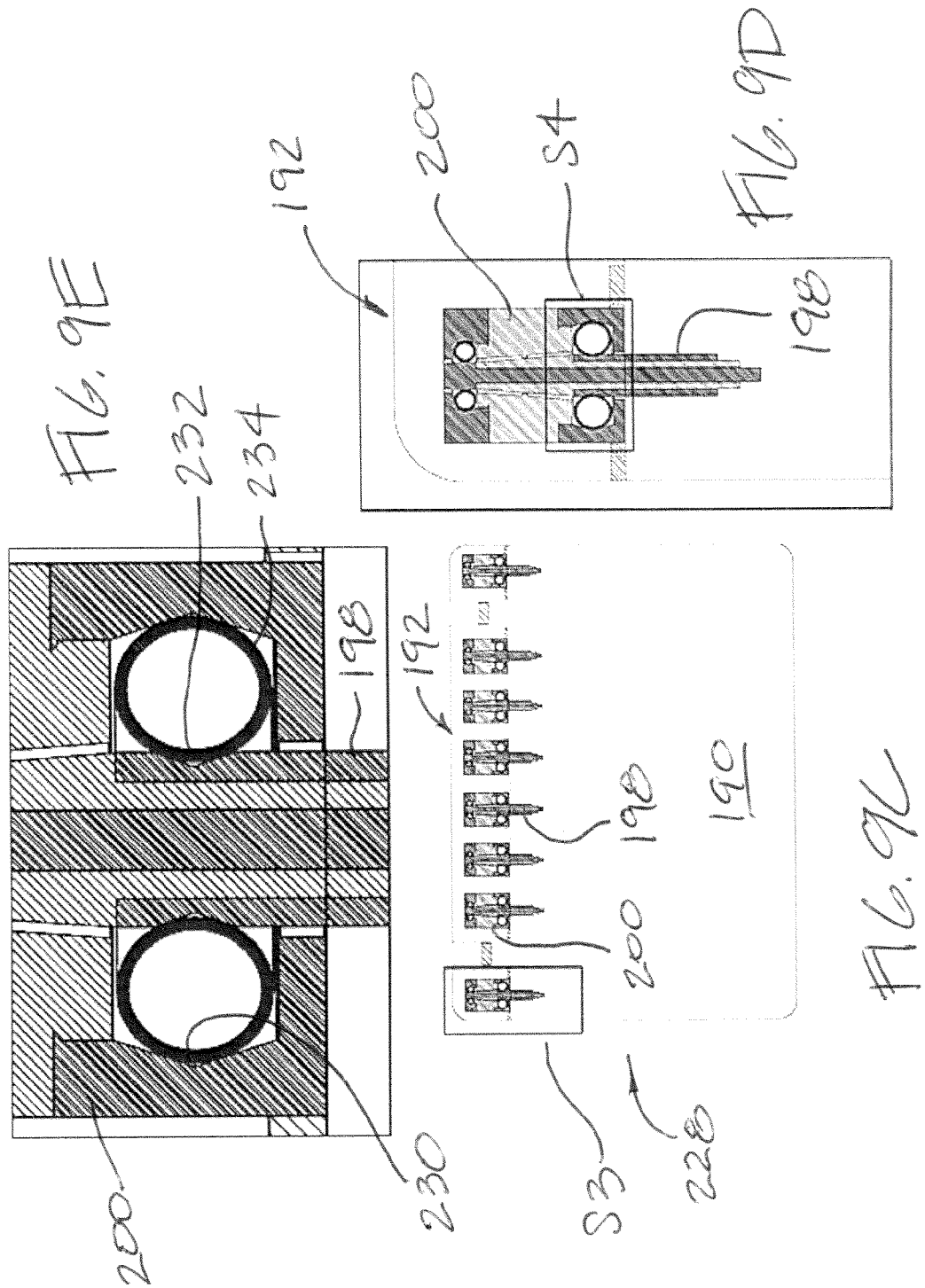

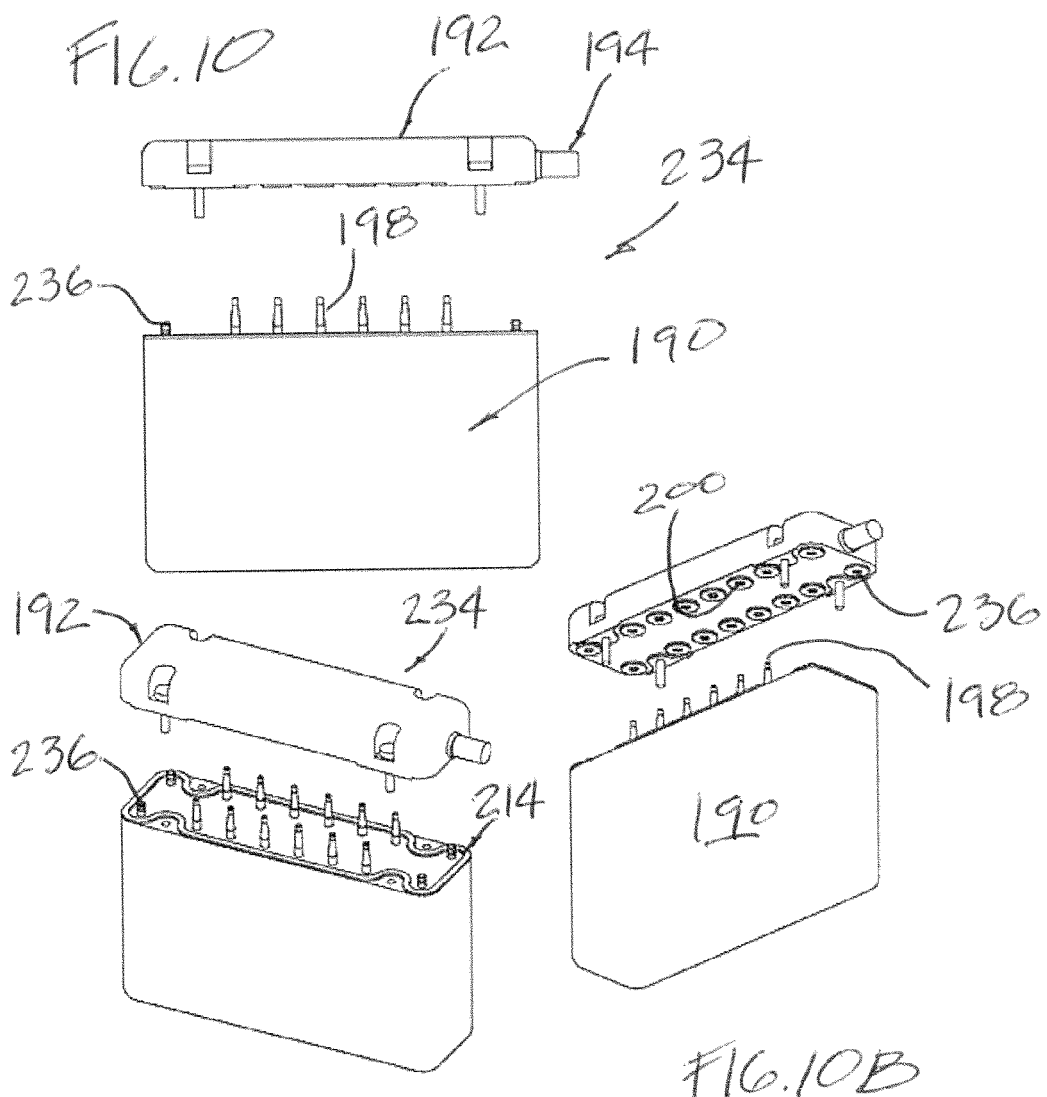

CONNECTORS WITH ELECTRICAL OR SIGNAL CARRYING CAPABILITIES AND RELATED METHODS

FIELD OF ART

The present disclosure pertains to the field of connectors, such as mechanical connectors with electrical or signal carrying capabilities and particularly to connectors with increased flow and/or path density. Devices, systems, and methods are disclosed in which connectors having multiple conductive paths for a given space are provided, which offer greater control and programming opportunities over connectors with more limited paths.

BACKGROUND

Connectors with springs for holding, latching, or locking applications are widely available for use as mechanical connectors and for use in electrical applications. Typically a pin is inserted into a bore of a housing and a spring is used therebetween as a connector for holding, latching, or locking application. Holding typically implies a single groove application, either in the pin or the housing, in which the spring force and the friction force between the spring and either the housing or the pin removably secure the two components together. Latching implies insertion to connect with removal capability to disconnect, without destroying the spring. Locking implies insertion to connect but without removal capability to disconnect unless the spring is destroyed. Both latching and locking applications typically use a groove on the pin and a groove in the housing to secure a spring therebetween.

Implantable medical devices for providing electrical stimulation to body tissues, for monitoring physiologic conditions, and for providing alternative treatments to drugs are well known in the art. Exemplary implantable medical devices include implantable cardio defibrillators, pacemakers, and programmable neuro-stimulator pulse generators, which are collectively herein referred to as "implantable medical devices" or IMDs. These IMDs typically incorporate a hermetically sealed device enclosing a power source and electronic circuitry, also known as a "can" or a "can housing". Connected to the sealed housing is a header assembly. The header assembly includes electrical contact elements that are electrically coupled to the electronic circuits or to the power source located inside the can via conductive terminals or leads. The header assembly provides a means for electrically communicating, via an external medical lead cable, between the electronic circuits or power source located inside the device and the actual stimulation point.

Industry wide standards have been adopted for, among other things, the dimensions, size, pin spacing, diameter, etc. for the receptacle and the medical lead cable. Furthermore, good electrical contact must be maintained during the life of the implantable medical device, and the medical lead cable for use with the IMD must not disconnect from the receptacle located in the header, yet be detachable for implanting and programming purposes and for replacing the IMD when necessary.

Although prior art connector contacts provide viable options for medical device manufacturers, the overall dimensions of existing receptacles pose manufacturing challenges. Among other things, placing stackable rings in between electrically insulating seals, positioning conductive contact elements in between conductive grooves for forming a receptacle and integrating the contact assembly into the IMD are difficult, costly and time consuming tasks.

Active implantable medical connectors have typically required serial arrays that allowed for several connections in a row. Examples of prior art connectors are disclosed in US Publication Nos. US2010/0233896 A1, US2008/0255631 A1 and US2008/0246231 A1, the contents of each of which are expressly incorporated herein by reference. As technology advances and new therapies require greater sophistication, the typical connection systems cannot support some of the new therapies that require high number of electrodes or connection nodes.

SUMMARY

Aspects of the present disclosure include a connector capable of carrying electrical or electric signal. The connector can comprise a first electrically conductive housing, a second electrically conductive housing and a housing sealing component at least partially isolating said first and second electrically conductive housings from each other; said first and second electrically conductive housings and housing sealing component defining a bore and defining a contact housing. A body, such as a pin, a rod, or an elongated member, is insertable into said bore. Said body can comprise a first electrical terminal and a second electrical terminal. A first electrically conductive spring is located in a first groove and a second electrically conductive spring is located in a second groove. Wherein said first electrically conductive housing, first spring, and said first electrical terminal defining at least a portion of a first electrical path. Wherein said second electrically conductive housing, said second spring, and said second electrical terminal defining at least a portion of a second electrical path.

Another feature of the connector wherein at least one of the first and second grooves is defined by a first groove on the inner surface of the bore and a second groove on the outer surface of the corresponding electrical terminal.

Another feature of the connector is a multi-part outer housing having a bore for receiving the contact housing.

Another feature of the connector wherein a portion of the inner surface of the bore and the corresponding portion of the outer surface of the body are tapered. This is understood to mean that the tapered surfaces can also be excluded.

Another feature of the connector wherein a non-conductive layer is provided between the first electrical terminal and the second electrical terminal.

Another feature of the connector wherein the first spring and the second spring are of the same size.

Another feature of the connector wherein the first spring and the second spring are of different sizes.

Another feature of the connector wherein an outer housing surrounds the combination first electrically conductive housing, second electrically conductive housing, housing sealing component, first conductive spring, and second conductive spring.

Another feature of the connector wherein a lead or wire is routed through the outer housing to contact the first electrically conductive housing or second electrically conductive housing.

Another feature of the connector wherein the portion of the inner surface of the bore between two consecutive electrically conductive springs and the corresponding portion of the outer surface of the body are tapered.

Another feature of the connector wherein the first sealing component is mechanically engaged with a second sealing component at least partially isolating the first and second electrical terminals from each other.

Another feature of the connector wherein the mechanical engagement of the first and second sealing components is accomplished by means of a latching feature.

Another feature of the connector wherein at least one of the first and second electrically conductive springs is a canted coil spring.

Another feature of the connector wherein at least one of the first and second electrically conductive springs is one of a garter spring and a ribbon spring.

Another feature of the connector wherein at least one of the first and second electrically conductive springs is a finger spring.

Another feature of the connector wherein the body is attached to a first structure and the combination first and second electrically conductive housing sections and the housing sealing component is attached to a second structure to put the first structure in electrical communication with the second structure.

Another feature of the connector wherein the first and the second structures are part of a land vehicle.

Another feature of the connector wherein the first and the second structures are part of a flying aircraft.

Another feature of the connector wherein the first and the second structures are part of a watercraft.

Another feature of the connector wherein the first and the second structures are part of a consumer electronic device.

Another feature of the connector wherein the first and the second structures are part of a train.

Another feature of the connector wherein the first and the second structures are part of a satellite.

Another feature of the connector wherein the first and the second structures are part of a device for performing a medical procedure.

Another feature of the connector wherein the first and the second structures are part of a wind turbine.

Another feature of the connector wherein the first and the second structures are part of a solar system.

A further aspect of the present disclosure is an array of at least two connectors capable of carrying electrical or electric signal. In some examples, each connector can comprise a first electrically conductive housing, a second electrically conductive housing and a first sealing component at least partially isolating said first and second electrically conductive housings from each other; said first and second electrically conductive housings and first sealing component defining a bore; a body insertable into said bore comprising a first electrical terminal and a second electrical terminal; a first electrically conductive spring in a first groove and a second electrically conductive spring in a second groove; said first electrically conductive housing and spring and said first electrical terminal defining at least a portion of a first electrical path, and said second electrically conductive housing and spring and said second electrical terminal defining at least a portion of a second electrical path.

Alternatively, each connector can comprise a first electrically conductive housing, a second electrically conductive housing and a housing sealing component at least partially isolating said first and second electrically conductive housings from each other; said first and second electrically conductive housings and housing sealing component defining a bore and defining a contact housing. A body, such as a pin, a rod, or an elongated member, is insertable into said bore. Said body can comprise a first electrical terminal and a second electrical terminal. A first electrically conductive spring is located in a first groove and a second electrically conductive spring is located in a second groove. Wherein said first electrically conductive housing, first spring, and said first electrical terminal defining at least a portion of a first electrical path. Wherein said second electrically conductive housing, said second spring, and said second electrical terminal defining at least a portion of a second electrical path.

Another feature of the array wherein, at least in one of the connectors, at least one of the first and second grooves is defined by a first groove on the inner surface of the bore and a second groove on the outer surface of the corresponding electrical terminal.

Another feature of the array wherein, at least in one of the connectors, at least a portion of the inner surface of the bore and the corresponding portion of the outer surface of the body are tapered.

Another feature of the array wherein, at least in one of the connectors, the portion of the inner surface of the bore between two consecutive electrically conductive springs and the corresponding portion of the outer surface of the body are tapered.

Another feature of the array wherein, at least in one of the connectors, the first sealing component is mechanically engaged with a second sealing component at least partially isolating the first and second electrical terminals from each other.

Another feature of the array wherein the mechanical engagement of the first and second sealing components is accomplished by means of a latching feature.

Another feature of the array wherein the length of the body of one of the connectors is different than the length of the body of another one of the connectors.

Another feature of the array further comprising at least one mechanical connector.

Another feature of the array wherein at least one of the first and second electrically conductive springs of at least one of the connectors is a canted coil spring.

Another feature of the array wherein at least one of the first and second electrically conductive springs of at least one of the connectors is one of a garter spring and a ribbon spring.

Another feature of the array wherein at least one of the first and second electrically conductive springs of at least one of the connectors is a finger spring.

A still yet further feature of the present disclosure is an assembly comprising a first component and a second component electrically coupled by means of a connector described elsewhere herein, which transfers electrical signals from one of the first and second components to the other one of the first and second components.

Yet another feature of the present disclosure is an assembly comprising a first component and a second component electrically coupled by means of an array described elsewhere herein, which transfers electrical signals from one of the first and second components to the other one of the first and second components.

An exemplary application of the disclosed connectors is in an implantable device. In some examples, the implantable device comprises a can housing, a header and at least one lead, said can housing and header being coupled by means of a connector described elsewhere herein, wherein the origin and end of the referred electrical paths are the can housing and the distal end of the at least one lead, respectively.

The implantable device further comprising a gasket seal to seal body fluids comprising a sealing band surrounding the connector.

The implantable device further comprising a gasket seal to seal body fluids comprising a sealing layer with an opening at the location of the connector.

Another feature of the implantable device wherein a printed circuit board in the header defines the portion of the referred electrical paths going from the connector to the at least one lead.

Another feature of the implantable device wherein a printed circuit board in the pulse generator defines the portion of the referred electrical paths going from the pulse generator to the connector.

Another feature of the implantable device wherein a printed circuit board in the header defines the portion of the referred electrical paths going from the connector to the at least one lead, and another printed circuit board in the pulse generator defines the portion of the referred electrical paths going from the pulse generator to the connector.

Another feature of the implantable device wherein the printed circuit board comprises two layers of printed circuits.

Another feature of the implantable device wherein at least one of the printed circuit boards comprises two layers of printed circuits.

Another feature of the implantable device wherein the body of the connector is attached to the header.

Another exemplary application of the disclosed connectors is in an array in an implantable device. In some examples, the implantable device comprises generator can housing, such as a pulse generator, a header and at least one lead, said pulse generator and header being coupled by means of the array described elsewhere herein, wherein the origin and the end of the referred electrical paths are the can housing and the distal end of the at least one lead, respectively.

Another feature of the implantable device with the array of connectors further comprising a gasket seal to seal body fluids comprising a sealing band surrounding the array of connectors.

Another feature of the implantable device with the array of connectors further comprising a gasket seal to seal body fluids comprising a sealing layer with an opening at the location of the connectors of the array.

Another feature of the implantable device with the array of connectors wherein a printed circuit board in the header defines the portion of the referred electrical paths going from the array of connectors to the at least one lead.

Another feature of the implantable device with the array of connectors wherein a printed circuit board in the pulse generator defines the portion of the referred electrical paths going from the pulse generator to the array of connectors.

Another feature of the implantable device with the array of connectors wherein a printed circuit board in the header defines the portion of the referred electrical paths going from the array of connectors to the at least one lead, and another printed circuit board in the pulse generator defining the portion of the referred electrical paths going from the pulse generator to the array of connectors.

Another feature of the implantable device with the array of connectors wherein the printed circuit board comprises two layers of printed circuits.

Another feature of the implantable device with the array of connectors wherein at least one of the printed circuit boards comprises two layers of printed circuits.

Another feature of the implantable device with the array of connectors wherein the body of at least one connector of the array is attached to the header.

A still yet further feature of the present disclosure is a method for forming a connector and a method for using the connector. In one example, the method for forming connector can comprise the steps of forming a contact housing by placing a housing sealing component in between a first electrically conductive housing section and a second electrically conductive housing section to at least partially isolate the first and second electrically conductive housing sections from each other; said first and second electrically conductive housing sections and housing sealing component defining a bore; assembling a first electrical terminal and a second electrical terminal together to form an insertable body; placing a first electrically conductive spring in a first groove defined at least in part by the first electrically conductive housing section; placing a second electrically conductive spring in a second groove defined at least in part by the second electrically conductive housing section; and placing the insertable body into the bore to form a first electrical path defined by the first electrically conductive housing section, the first electrically conductive spring, and the first electrical terminal and a second electrical path defined by the second electrically conductive housing section, the second electrically conductive spring, and the second electrical terminal.

Another feature of the method for forming further comprising placing a non-conductive layer between the first electrical terminal and the second electrical terminal to isolate the first and second electrical terminals from one another.

Another feature of the method for forming further comprising placing the contact housing adjacent two or more contact housings to form an array.

Another feature of the method for forming further comprising placing the insertable body adjacent two or more insertable bodies to form an array.

Another feature of the method for forming further comprising attaching the contact housing to a first structure and attaching the insertable to a second structure.

Another feature of the method for forming wherein the first structure and the second structure is part of a flying aircraft, a land vehicle, a watercraft, a medical device, a consumer electronic device, a wind turbine, or a satellite.

BRIEF DESCRIPTION OF DRAWINGS

The foregoing features and other features of the disclosure will now be described with reference to the drawings of the various embodiments. In the drawings, the same components have the same reference numerals. The illustrated embodiments are intended to illustrate, but not to limit the disclosure.

FIGS. 4 to 4A show an alternative implantable device, similar to that of FIGS. 3-3E, but with two receiving bores for receiving two leads.

FIGS. 6 to 6B show an implantable device, which is similar to that illustrated in FIGS. 3 to 3E, wherein the bodies, such as pins or projections, are insertable into the bores of the connectors of the array, which are attached to or are located with the header.

FIGS. 7 to 7C show an implantable device, which is similar to that illustrated in FIGS. 3 to 3E, wherein the bodies, such as pins or projections, and the bores are located on both the header and the can housing, in even numbers or, as shown, un-even numbers.

FIGS. 8 to 8f show an implantable device, which is similar to that illustrated in FIGS. 3 to 3E, wherein the body length of some connectors of the array differ from the body length of the rest of the connectors of the array.

FIGS. 9 to 9e show and implantable device, which is similar to that illustrated in FIGS. 3 to 3E, wherein at least one of the connectors of the array comprises latching features.

DETAILED DESCRIPTION

The detailed description set forth below in connection with the appended drawings is intended as a description of the presently preferred embodiments of connectors with electrical or signal carrying capabilities provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
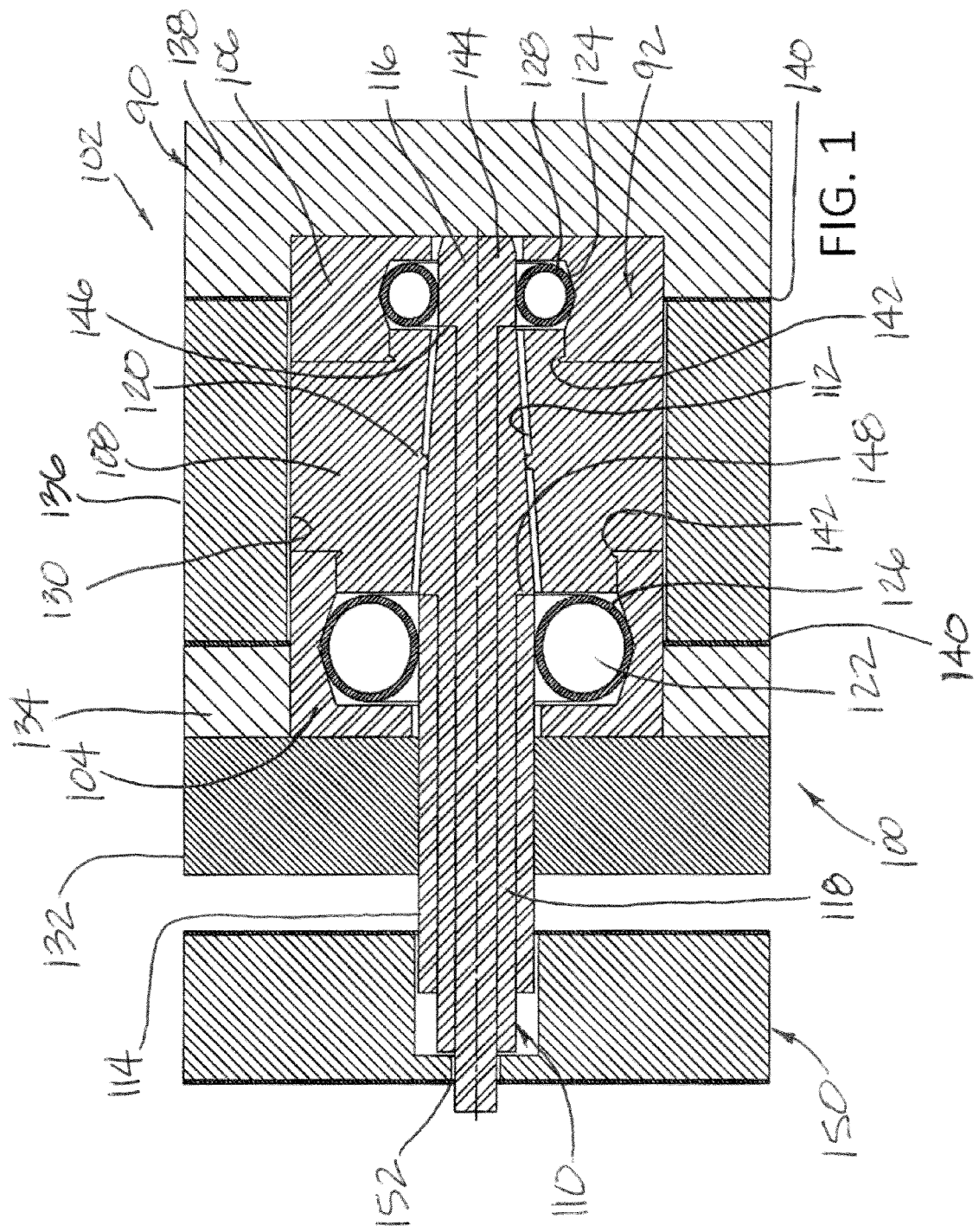
FIGS. 1 to 2C show several different connectors each comprising a body, such as an elongated pin, a shaft, a rod, or an elongated member, which can be symmetrical or non-symmetrical, inserted into a bore and at least two electrically conductive springs electrically coupling the outer surface of the body and the inner surface of the bore. The body and the bore of each connector can separately connect to wires or other electrical sources and operate as a stand-alone connector or form part of a larger array comprising multiple bodies and multiple bores forming multiple connectors in an array.

FIG. 1 shows a connector assembly 100, which may simply be referred to as a connector, comprising an electrically conductive housing or contact housing 102 comprising an outer housing section 90, also called simply a second housing, and an inner housing section 92, also called simply a first housing. The inner housing section 92 comprises a first conductive housing section 104 and a second conductive housing section 106 separated from one another by a housing sealing component 108, which isolates the two conductive sections from each other. Both electrically conductive housing sections 104, 106 and the sealing component 108 are mechanically engaged and define a common bore 112 for receiving a body 110, such as a pin, a shaft, or an elongated member for inserting into a bore.

The body 110 is inserted into the bore 112 and in the embodiment shown comprises two electrical terminals or electrically conductive parts 114, 116 isolated from each other by a body sealing component 118. In the example shown, both sealing components 108, 118 are mechanically engaged, such as by providing a raised projection or bump 120 in the bore 112 for engaging the surface of the body sealing component 118. In another embodiment, the bump 120 is located on the surface of the body sealing component 118 for engaging the surface of the housing sealing component 108. The body sealing component 118 can vary in thickness, length and shape. If two contact springs are use, the two electrical terminals are sized so that they separately contact each corresponding spring.

Two grooves 122, 124 are provided in the housing 102 to receive two electrically conductive canted coil springs 126, 128. As shown, one groove 122 is formed by part of the first conductive housing section 104 and the housing sealing member 108, which defines a first groove for receiving the spring, the other groove 124 is formed by part of the second conductive housing section 106 and the housing sealing member 108, which defines a second groove for receiving the spring 128. To facilitate installation, the first groove 122 is larger than the second groove 124, which allows the smaller canted coil spring 128 to be inserted into the bore and installed in the second groove 124 before installing the second larger canted coil spring 126 into the first groove 122. However, if there is no taper bore, then similar sized grooves and springs may be used. The grooves may have different groove bottom configurations, such as V-bottom, slanted bottom, or flat bottom; and may have different sidewall configurations, such as two sidewalls that converge, that diverge, or that are generally parallel. One wall can be generally perpendicular to the axis of the contact housing while the other tapers. Each groove may also be made entirely from a single structure, such as being formed entirely from the first conductive housing section or the second conductive housing section, or as a composite by having at least a portion of the groove being formed by an adjacent structure, such as by the adjacent sealing component. One electrically conductive canted coil spring 126 electrically couples one electrically conductive housing section 104 and one electrical terminal 114, which together define a portion of a first electrical path. The other electrically conductive canted coil spring 128 electrically couples the other electrically conductive housing section 106 and the other electrical terminal 116 together to define a portion of a second electrical path. The first and second electrical paths may carry similar or different electrical signals or currents. In other words, two different leads (not shown) may be connected to the first and second conductive housing sections 104, 106 for carrying electrical signals or currents to or from the two conductive housing sections, through the two canted coils springs 126, 128, and through the two electrical terminals 114, 116 on the body 110, which may be connected to electrodes or leads (not shown).

In the embodiment shown, the bore defined by the housing sealing member 108 is tapered so that the bore section closest to the first groove 122 is larger than the bore section closest to the second groove 124. Similarly, the body sealing component 118 is sized and shaped to comply with the tapered bore and is therefore also tapered. However, a straight bore is also contemplated, as further shown with reference to FIGS. 2-2C.

As shown, the outer housing section 90 defines a bore 130 for receiving the inner housing section 92. In one example, the outer housing section 90 comprises four different outer housing sub-sections 132, 134, 136, 138 assembled together to define the bore 130 for receiving the inner housing section 92. The housing sub-section 132 has an opening sized to form fit or seal against the body 110. The four outer housing sub-sections may incorporate detents, latches, or other fastening means, such as bolts, nuts, threaded bores, etc., for securing the different sections together. In yet another embodiment, a high temperature, thermally stable, epoxy or bond material may be used to secure the outer housing components together. Alternatively or in addition thereto, a thermoplastic encapsulation layer, a thermoplastic rubber outer layer, or a thermoplastic elastomer outer layer may be placed over the outer housing 90 to retain the outer housing therein. In the example shown, outer housing sub-section 134 and outer housing sub-section 138 are made from a conductive material to electrically conduct with the inner first and second conductive housing sections 104, 106. Outer housing sub-section 136 is made from a non-conductive material to isolate outer housing sub-section 134 from outer housing sub-section 138 so as to avoid cross-signaling or short circuiting. Outer housing sub-section 132 may be made from the same or different non-conductive material as outer housing sub-section 136. In an alternative embodiment, the inner housing 92 may function as a standalone contact housing without utilizing the outer housing 90. For example, the various components of the inner housing may use latching features or adhesive, such as high temperature resistant bond, to secure the components together. Thus, the inner housing 92 alone may define a contact housing for use with the body without the outer housing.

Exemplary conductive materials usable with the present connector includes copper, copper alloy, silver, silver alloy, gold, gold alloy, aluminum, aluminum alloy, steel (carbonized), brass, brass alloy, bronze, bronze alloy, and stainless steel. The canted coil spring may be made from a single material or metallurgy or may be cladded or coated with two or more layers. Exemplary springs usable in the present connector include those disclosed in co-pending application No. US 2010/0289198, Ser. No. 12/767,421, filed Apr. 26, 2010, the contents of which are expressly incorporated herein by reference.

In another example, the outer housing 90 may be made from fewer than four housing sections and may have less than two conductive outer housing sections. For example, conductive leads or wires (not shown) may be routed through the seams 140 to contact the first and second conductive housing sections 104, 106. Thus, the outer housing 90, when incorporated, may also be made wholly from a non-conductive material by routing wires or cables through the outer housing wall to couple to the conductive surfaces of the inner housing 93.

To increase contact surface areas or points between the inner housing 92, and more specifically between the two grooves 122, 124, and the springs, V-grooves are provided. The V-grooves or V-bottom surfaces increase the contact points with the springs, as compared to a flat bottom surface contacting a spring. In another example, a flat groove bottom is provided between the two tapered V-surfaces, also forming V-grooves, with a slightly flat apex. In other examples, the grooves can have a single taper bottom wall or a flat bottom wall. In still other examples, the coils of the two canted coil springs are dimpled or provided with bent sections to further increase contact surface areas with the grooves. Exemplary canted coil springs with these configurations are provided in co-pending publication No. US 2012/0174398, Ser. No. 13/315,759, filed Dec. 9, 2011; and in co-pending publication No. US 2011/0062640, Ser. No. 12/882,797, filed Sep. 15, 2010, the contents of which are expressly incorporated herein by reference. As understood from the noted applications, canted coil springs can include radial canted coil springs and axial canted coil springs. Both canted coil spring types have coils that are canted generally along the same direction and each comprising a major or longer axis and a minor or shorter axis. In other examples, the springs can have different wire cross-sections than round and the coils can have different shapes than elliptical or oval.

The grooves 122, 124 have groove side walls that are both conductive and non-conductive, as one of the sidewalls of each groove is formed by the middle seal section 108, which is made from a non-conductive material. As shown, the middle seal section 108 projects into the two adjacent conductive housing sections 104, 106 to form part of the two grooves. The seal and the two adjacent conductive housing sections 104, 106 can have a simple slip fit. As shown, the seal 108 has a notch 142 at each end for engaging a projection on each conductive housing section to form a latched engagement on each end. In other examples, the conductive housing sections 104, 106 each comprises a complete groove, which is understood to include a bottom wall and two side walls, which is entirely conductive. For example, the housing sections 104 can be machined or cast with a groove having a bottom wall located between two sidewalls.

With reference again to the body 110 of FIG. 1, the end external of the bore 112 of the housing is exemplary only. In other words, the end can be located inside a sleeve and extended to a far end for connecting to a circuit board, an electrical source, wires or electrodes. At the terminal end with the electrical terminal 116, the body comprises an enlarged tip 144 comprising a shoulder 146 for seating the body sealing component 118, which also has a shoulder 148 for seating the outer electrical terminal 114.

A cap 150 is shown comprising a bore 152. The cap 150 may be part of a header or other objects that incorporate the disclosed connector 100. In other examples, the cap 150 may be omitted.

The connector assembly 100 of FIG. 1, as well as the other figures discussed elsewhere herein, may be used as a mechanical connector to secure two or more objects or structures together or for both mechanical connection with electrical or signal carrying. For example, the connector 100 may be used with an implantable medical device to carry electrical signals from between a can housing, which houses the electronics and power, and a plurality of electrode pads positioned remotely from the can housing and connected to the can housing by a lead cable. The connector 100 may also be used to connect two different electrical sources or nodes in an automotive, oil and gas, aerospace, consumer electronics, green energy, medical technology, and other applications that require connections between two electric or signal carrying sources or nodes. For example, the body 110 can be connected to one source or node and the contact housing 102 to another source or node that electrically communicate with one another when the body is inserted into the bore of the contact housing 100.

Figure 1A:
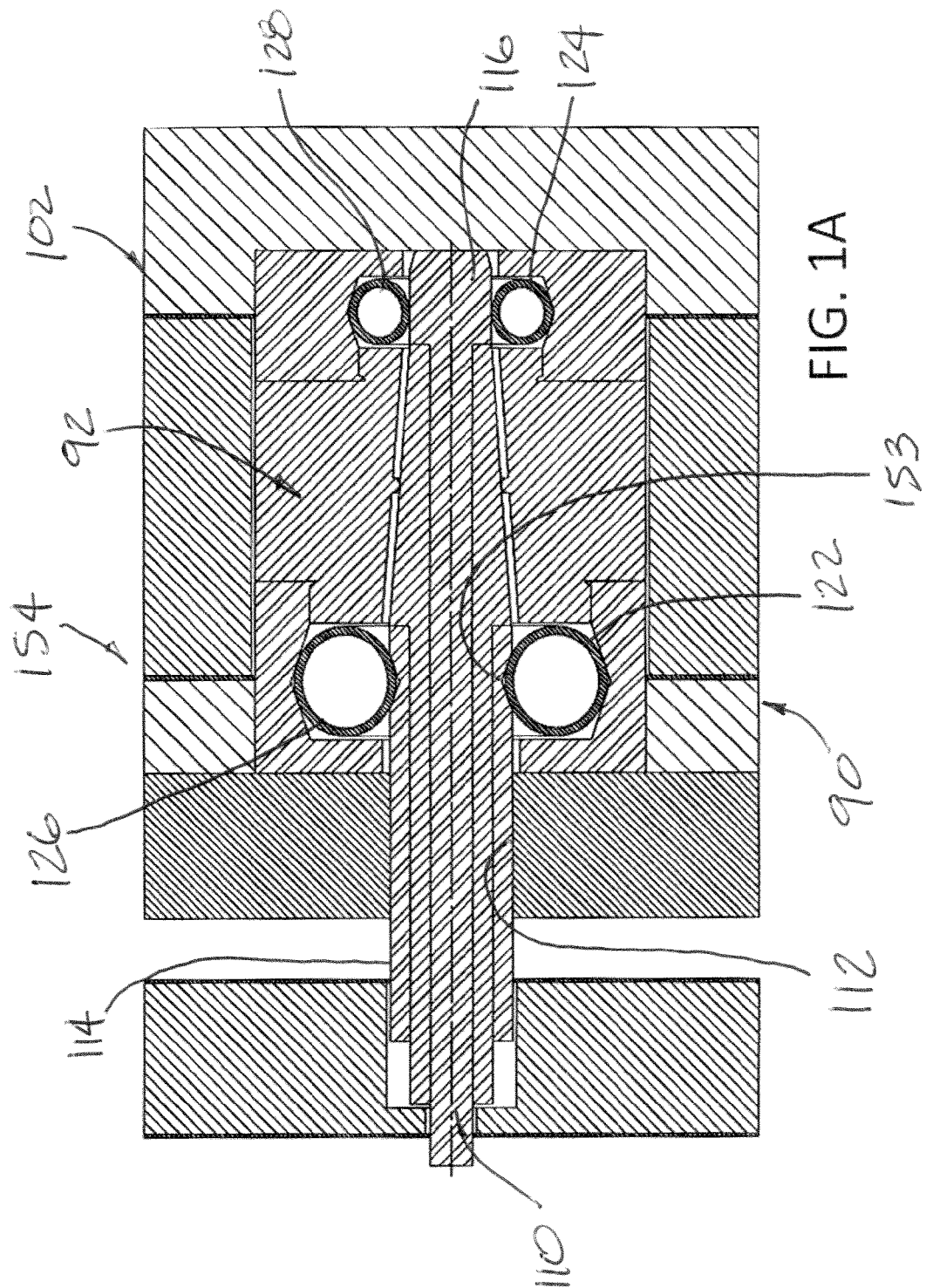

FIG. 1A shows a connector 154 that is substantially similar to the connector 100 of FIG. 1. As shown, the outer electrical terminal 114 of the body 110 is provided with a recess 153 for receiving or accepting part of the spring 126. In one example, the recess 153 is generally arcuate. In another example, the recess 153 is a V-groove. The recess 153 and the housing groove 122 together defines a latch when capturing the spring 126 therebetween to increase the force needed to remove the body 110 from the bore 112. In an alternative embodiment, the recess 153 is formed on the inner conducive terminal 116 to capture the inner spring 128 with the inner housing groove 124. In still yet another example, two recesses 153 are provided on the body 110, one on the outer electrical terminal 114 and one on the inner electrical terminal 116 to form two latch points.

Thus, as provided herein, the present connector comprises a housing comprising a bore comprising a first housing groove made, at least in part, from a conductive material spaced from a second housing groove made, at least in part, from a conductive material and having a non-conductive material located therebetween to isolate the two conductive materials, at least in part, from one another. The housing comprising a common bore for receiving a body comprising a first electrical terminal and a second electrical terminal having a non-conductive surface therebetween. The connector further comprises a first canted coil spring in contact with both the first housing groove and the first electrical terminal and a second canted coil spring in contact with both the second housing groove and the second electrical terminal. In an example, the first housing groove, the second housing groove, and the non-conductive material located therebetween define a contact housing and located or positioned in a bore of an outer housing. In some example, the outer housing as an inlet for receiving the contact housing and a cap having an opening aligned with the common bore.

To increase the removable force to remove the body from the housing, a groove is provided on the body to latch with the first canted coil spring or the second canted coil spring.

To simplify manufacturing, the outer housing may be made from fewer than two outer housing components or sections. Wires or conductors may be placed through the wall of the simplified outer housing to contact the structures defining the first housing groove and the second housing groove. In an alternative embodiment, the outer housing is omitted and the inner housing is a standalone contact housing for use with the body.

The present disclosure is further understood to include a method for making the disclosed connector and a method for using the disclosed connector. Another feature of the present disclosure is a method for sizing springs to operate with at least two grooves of each contact housing. For example, the springs can be sized, shaped, and/or configured to work in parallel or in series when mounted in at least two adjacent grooves inside a single contact housing. In another example, the springs are sized, shaped, and/or configured to work in parallel or in series when mounted in at least two adjacent grooves inside a single contact housing and wherein the two adjacent grooves have different groove sizes.

Figure 1B:
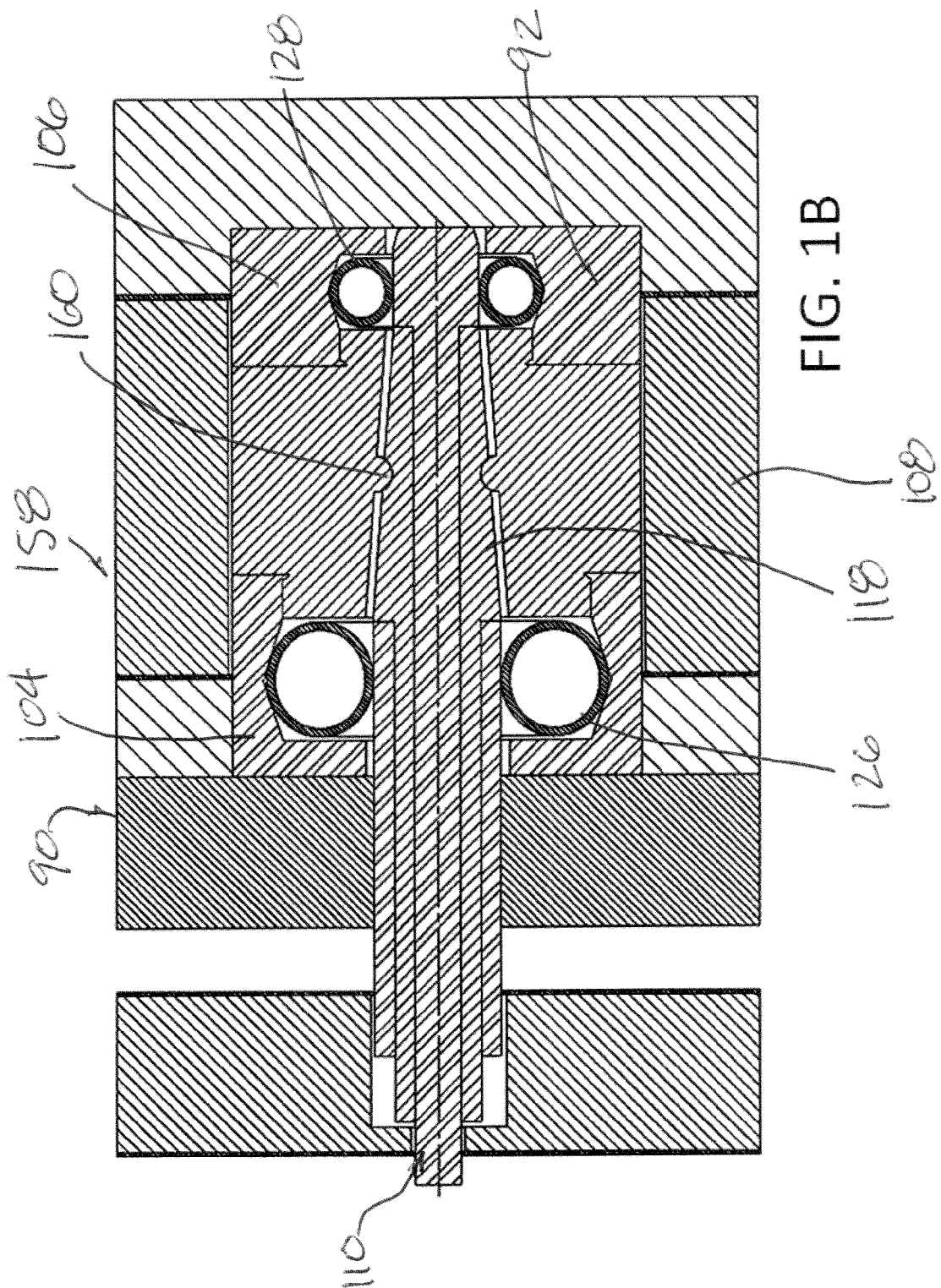

In still another example, the disclosed connector is used in a system, such as in an implantable medical device, in a car, in a computer, in an aircraft, in a watercraft, etc. Thus, the disclosed connector may be used in combination with other connectors to provide an array for transmitting multiple electrical signals. In its simplest form, the disclosed connector is capable of carrying at least two electrical signals to or from the contact housing having a single bore FIG. 1B shows a connector 158 provided in accordance with another aspect of the present disclosure. The connector 158 is similar to the connector 100 of FIG. 1 but wherein a latching feature 160 is provided between the housing seal 108 and the body sealing component 118. The latching feature 160 mechanically engages the housing seal 108 and the body sealing component 118 together. As shown, a projection is provided on the housing seal 108 and a groove is provided on the body sealing component 118. In another example, the location of the groove and the projection are reversed.

Figure 1C:
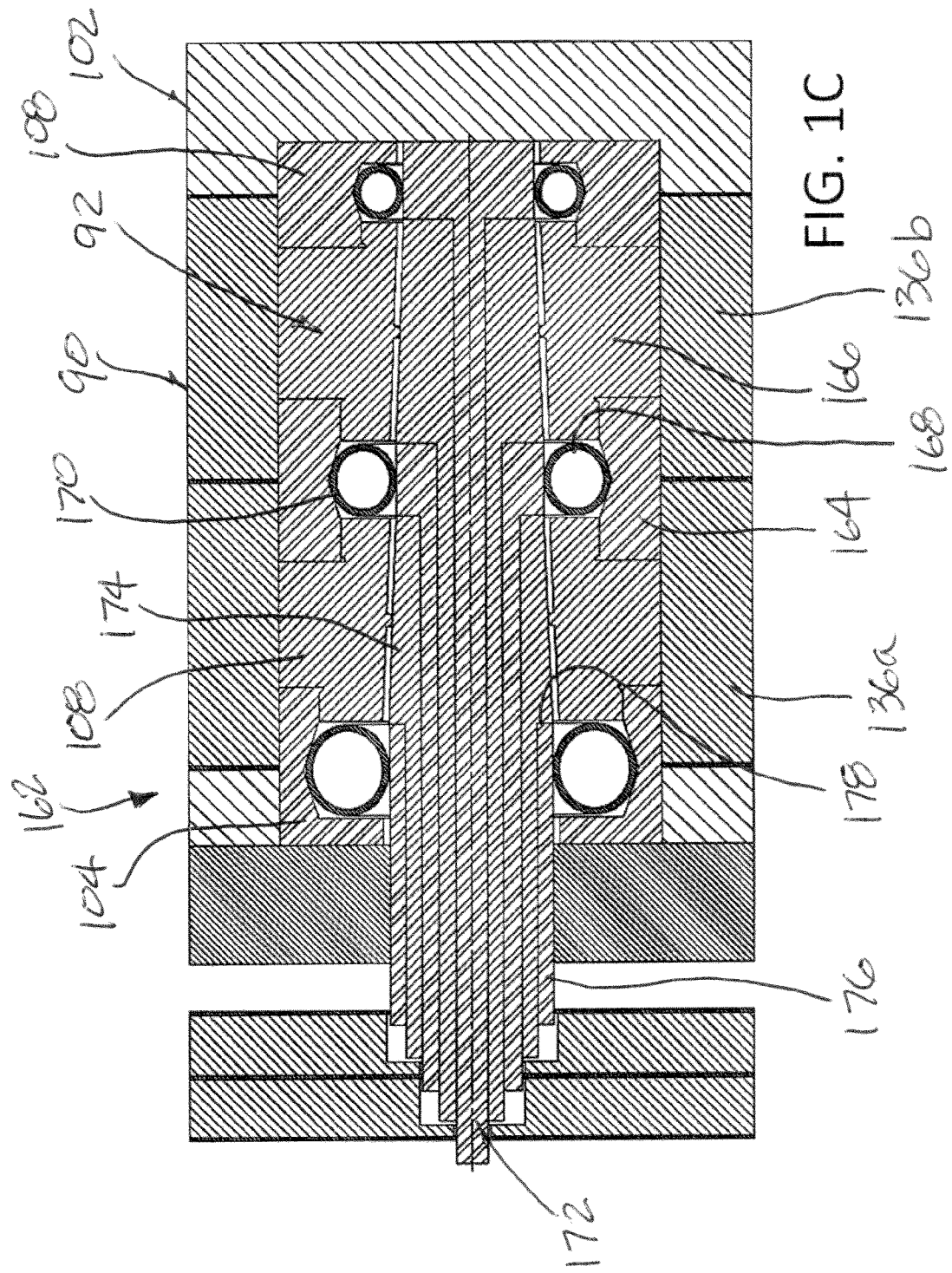

FIG. 1C shows a connector 162 provided in accordance with another aspect of the present disclosure. The connector 162 shares some similarity with the connector 100 of FIG. 1 with a few exceptions. As shown, the inner housing section 92 is provided with an additional electrically conductive housing section 164. The electrically conductive housing section 164 is generally cylindrical and comprises two open ends and an internal recess, such as a V-groove. To isolate the conductive housing section 164 from the other conductive housing sections 104, 108, an additional inner housing sealing section 166 is provided. The conductive housing section 164 has two sealing sections 108, 166 forming sidewalls to define a groove 170, such as forming a third housing groove, to receive an additional canted coil spring 168.

The outer housing 90 can have the same number housing components as that of FIG. 1. However, as shown, the middle outer housing section 136 is parsed into two separate sections 136a, 136b to facilitate assembly. In other examples, fewer outer housing components are contemplated.

The body 172, such as a pin or shaft, has been modified to incorporate three total electrical terminals for contacting the three springs positioned in the housing 102. As shown, a second body sealing component 174 is provided with a shoulder 178 for seating a third electrical terminal 176. The additional electrically conductive canted coil spring 168 electrically couples the additional electrically conductive housing 164 to form a connector housing having three conductive paths with three different canted coil springs to conduct across a body, such as a pin or an elongated member, with three electrical terminals. The three conductive inner housing components forming, at least in part, the three grooves are each in contact with at least one non-conductive component, such as a non-conductive seal section having a bore. Similarly, the three electrical terminals on the body are each in contact with at least one non-conductive body sealing component. As shown, each body sealing component comprises a shoulder for seating a terminal.

In one example, canted coils springs are utilized for the connectors of FIGS. 1, 1A, 1B, and 1C. In another example, the canted coil springs may be replaced by garter springs, ribbon springs, finger springs or other suitable types of spring.

The connector 180 of FIG. 2 is similar to the embodiment of FIG. 1 except the inner surface of the bore 112 and the outer surface of the body 110 do not comprise tapered portions.

Figure 2A:
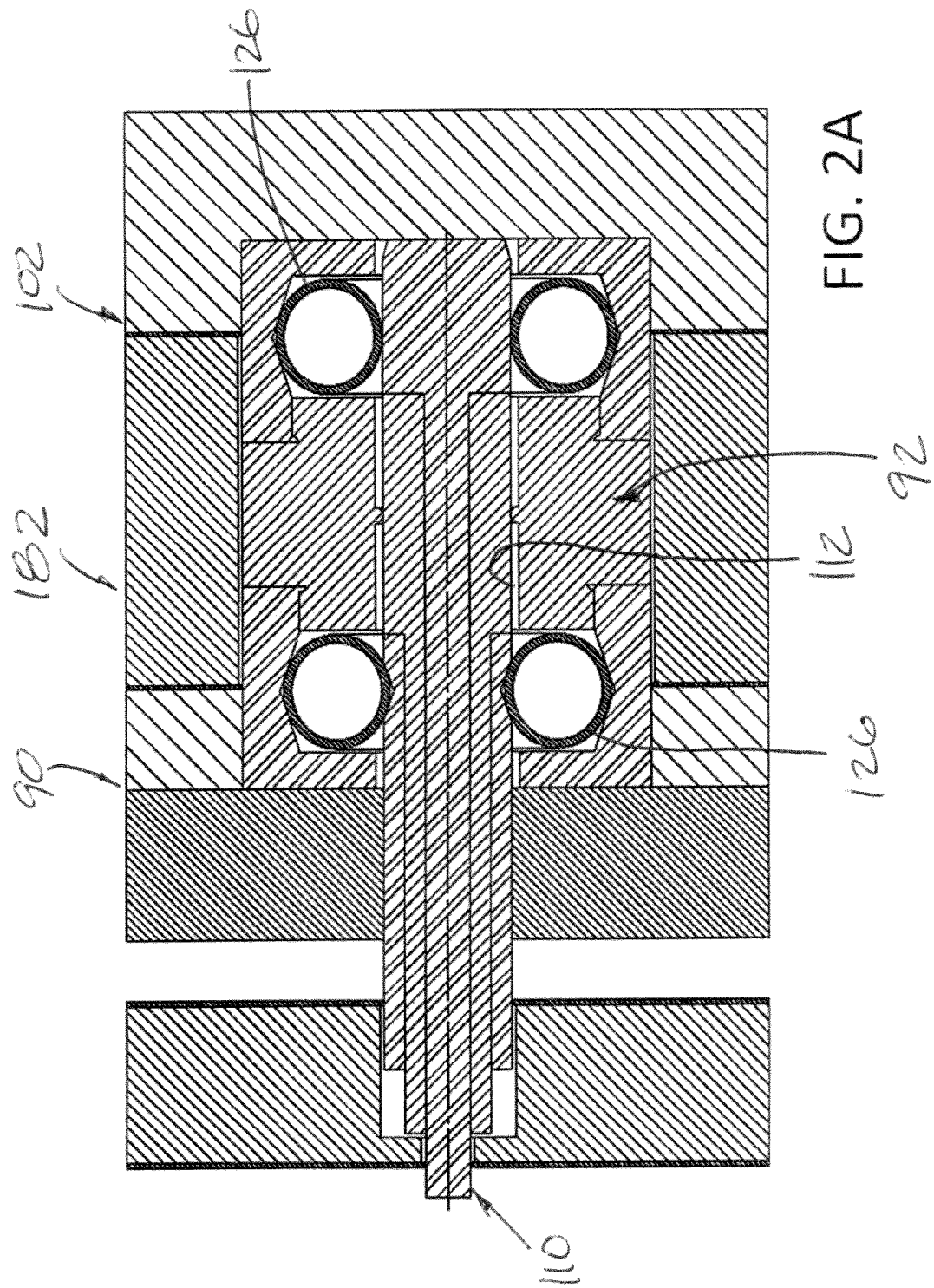

The connector 182 of FIG. 2A is similar to the embodiment of FIG. 1A except the inner surface of the bore 112 and the outer surface of the body 110 do not comprise tapered portions.

Figure 2B:
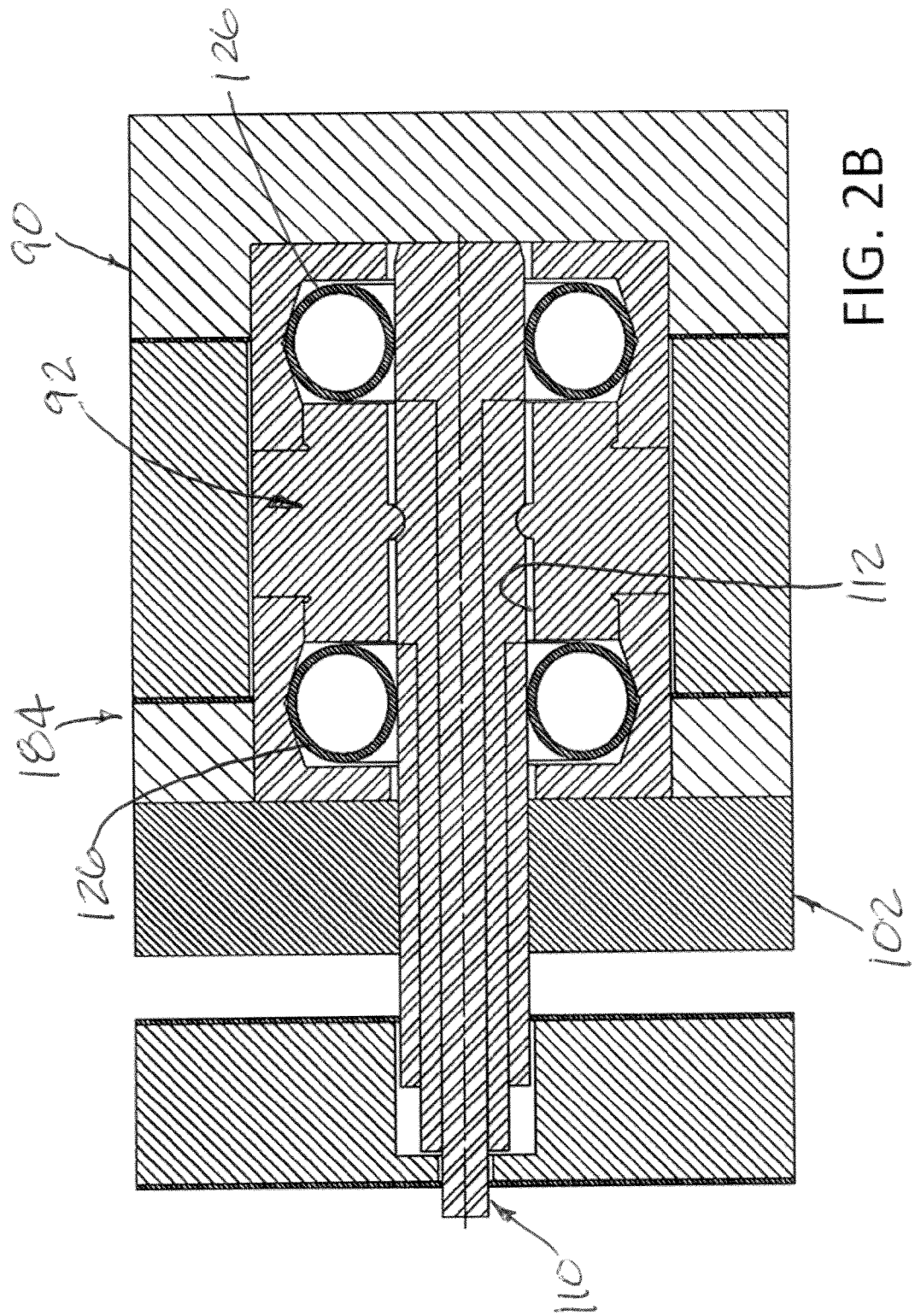

The connector 184 of FIG. 2B is similar to the embodiment of FIG. 1B except the inner surface of the bore 112 and the outer surface of the body 110 do not comprise tapered portions.

Figure 2C:
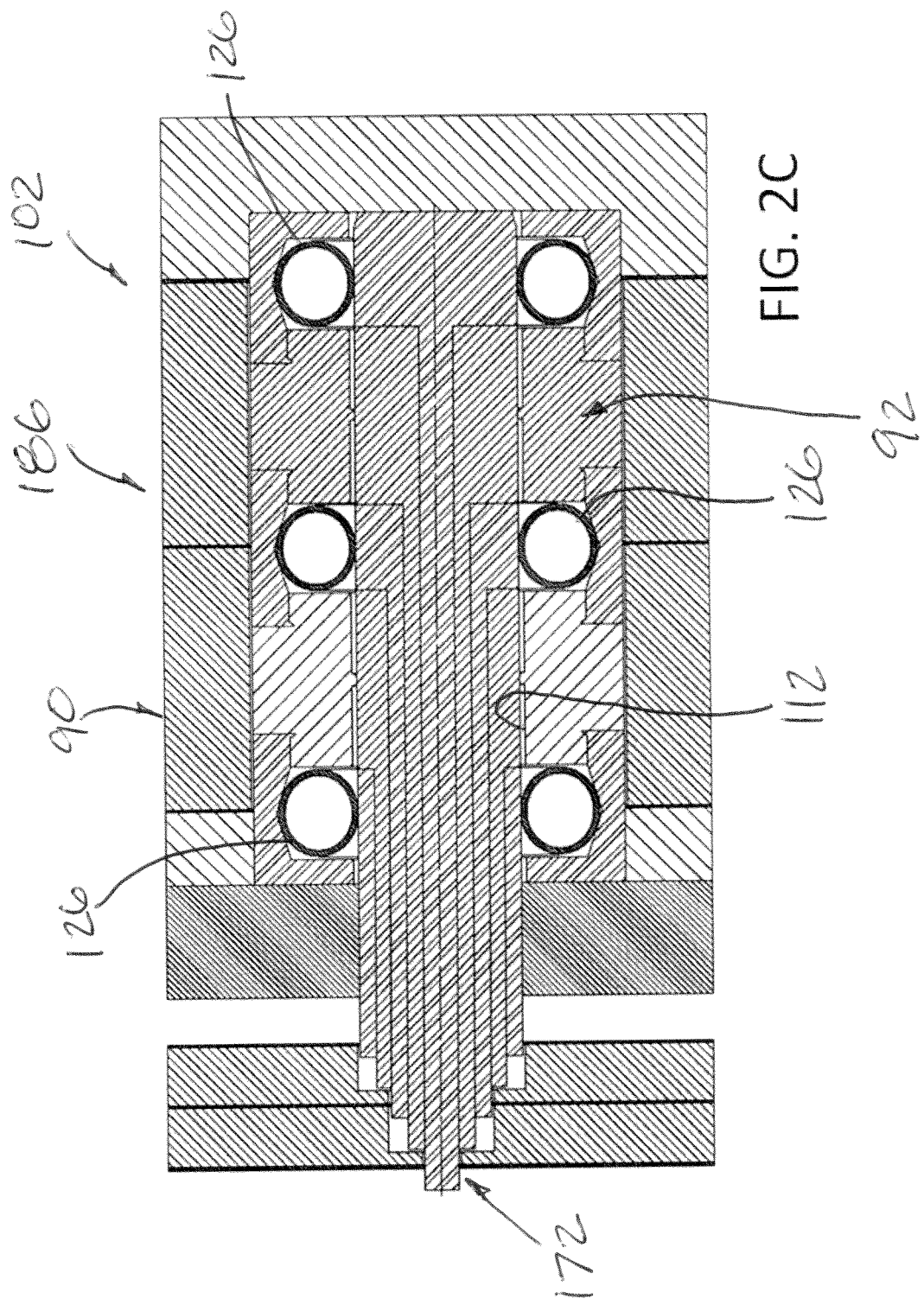

The connector 186 of FIG. 2C is similar to the embodiment of FIG. 1C except the inner surface of the bore 112 and the outer surface of the body 172 do not comprise tapered portions.

Figures 3, 3A:
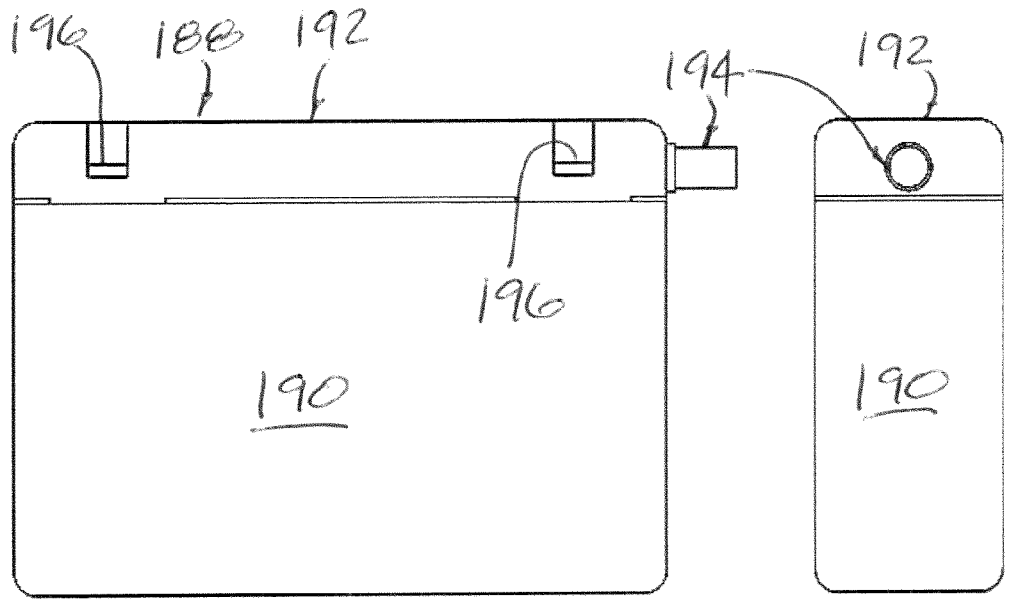
FIGS. 3 to 3E illustrate an implantable device in various stages of assembly or disassembly. The device comprising a can housing, such as a pulse generator, a header and one lead, which can have multiple electrodes bundled therein. The can housing and the header are coupled together with an array of connectors each comprising a body, such as a pin, a shaft, or an elongated member, inserted into a bore having at least two electrically conductive springs electrically coupling the outer surface of the body and the inner surface of the bore.

FIG. 3 is a side view of an implantable medical device 188 (IMD) provided in accordance with aspects of the present disclosure. The IMD 188 is provided with a can housing 190, a header 192, and a lead cable 194 inserted into the bore of the header to electrically contact the electrode leads located inside the lead cable 194 with an array of connectors, such as one of the connectors shown in FIGS. 1-2C. One or more fasteners 196 are incorporated to fastened the header 192 to the can housing 190. In practice, the gaps for the exposed fasteners 196 can be back-filled with an implantable sealer. Exemplary IMDs are further disclosed in co-pending publication No. 2008/0246231, Ser. No. 12/062,895, filed Apr. 4, 2008, the contents of which are expressly incorporated herein by reference.

FIG. 3A shows an end view of the IMD 188 of FIG. 3.

Figures 3B, 3C:
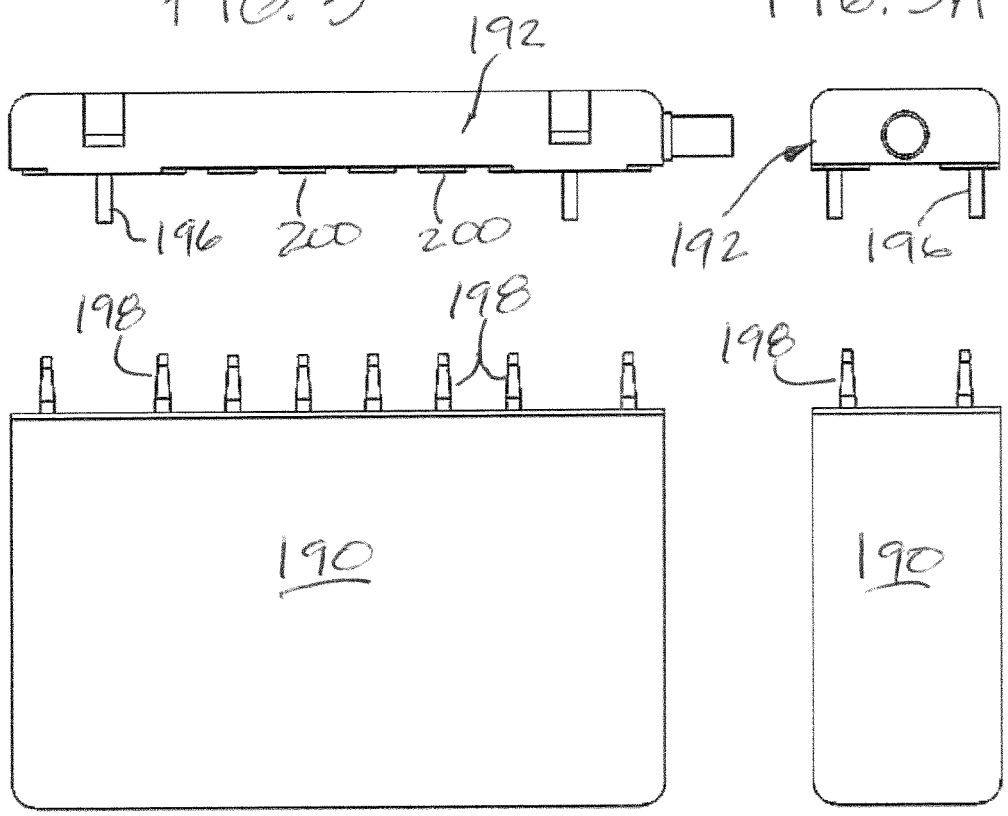

FIG. 3B is a partial exploded side view of the IMD 188 of FIG. 3 and FIG. 3C is a partial exploded end view of the IMD of FIG. 3, which show the header 192 spaced from the can housing 190. In the present two views, a plurality of bodies 198, such as pins or elongated insertable members, are connected to the can housing 190 while a plurality of contact housings 200 are connected to the header 192 for receiving the bodies. The bodies may be one of the bodies disclosed in FIGS. 1-2C and the contact housings 200 may be one of the housings disclosed in FIGS. 1-2C. The origin and end of the electrical paths associated with each contact housing are the IMD, which can be a pulse generator, and the origin and end of the electrical paths associated with each body are the distal end of the lead 194.

FIG. 3D is a partial exploded perspective view of the IMD 188 of FIG. 3. As shown, the pluralities of contact housings 200 are formed in an array comprising two rows located near the two side edges 202 and between the two end edges 204 of the header 192. The contact housings 200 are spaced generally in a pattern to maximize their numbers on the header. The bodies 198 are similarly arranged on the can housing 190 so as to project into corresponding bores of the contact housings. As further discussed below, each body 198, whether comprising two contact terminals or more as disclosed in FIGS. 1-2C, is wired to corresponding leads located inside the can housing 190, which are wired to circuitries located inside the can housing. The circuitries enable signals to transfer between the controller located inside the housing 190 to the lead cable 194 via the connectors, which comprise the plurality of bodies 198 and contact housings 200. On the header, each pair of conductive contact housing sections and conductive spring for each contact housing 200 is routed or wired to a terminal presented in the bore of the header 192. This allows the electrodes located in the lead cable 194 to contact the terminals in the bore. As further discussed below, the various leads or wire ends may be terminated with a printed circuit board (PCB).

As shown, there are sixteen (16) connectors having sixteen bodies 198 and sixteen contact housings 200. If each contact housing 200 has two contact springs, similar to the contact housing 102 shown in FIG. 1, then the IMD has at least thirty-two (32) contact paths in which to transmit signals. If each contact housing 200 has three contact springs, similar to the contact housing 102 shown in FIG. 1C, then the IMD as at least forty-eight (48) contact paths in which to transmit signals. However, in some embodiments, the contact housings may have a single contact spring or more than three contact springs so that the potential contact paths can vary from at least 16 to more than forty-eight. However, these numbers are exemplary only and that different number of connectors may be incorporated and the number of contact points for each connector can vary.

FIG. 4 is a partial exploded view of an IMD 210 and FIG. 4A is an assembled perspective view of an IMD 210 provided in accordance with another aspect of the present disclosure. The IMD 210 is similar to the IMD 188 of FIGS. 3-3E with the exception of the header 212, which has two bores for receiving two lead cables 194. This allows for one row of contact housings 200 to be wired or routed to one set of terminals inside the header 212 and the second row of contact housings 200 to be routed to a second set of terminals inside the header 212. The number of electrical paths can thus be divided between two sets of terminals to contact two different lead cables 194, which minimize the number of electrodes in each lead cable, as compared to the lead cable of FIGS. 3-3E.

Figure 5A:
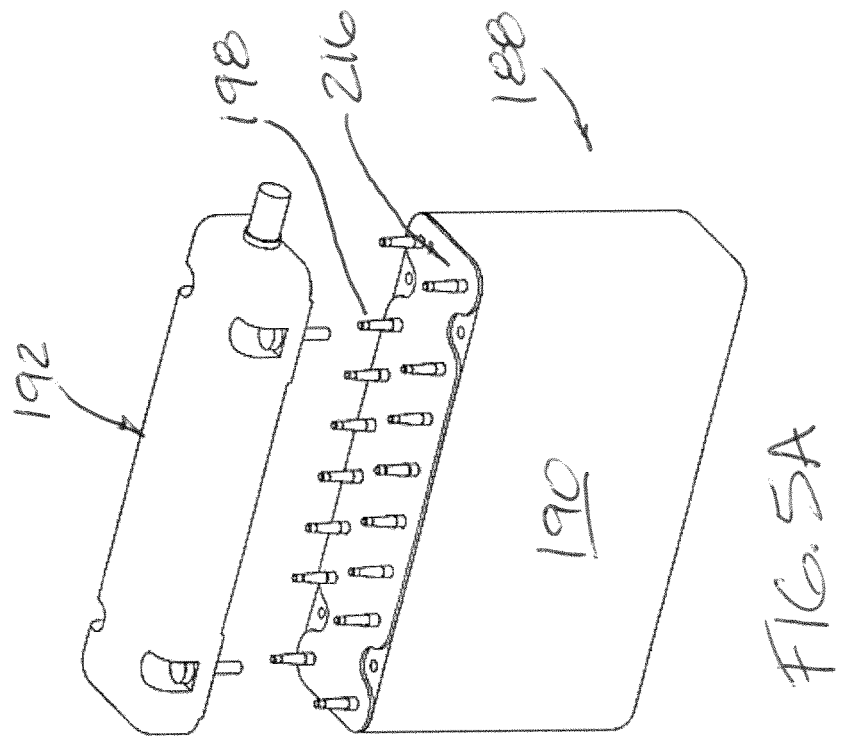
FIGS. 5 and 5A show two possible gasket seals for sealing the seam between the header and the can housing to seal the device from body fluids.
Figure 5:
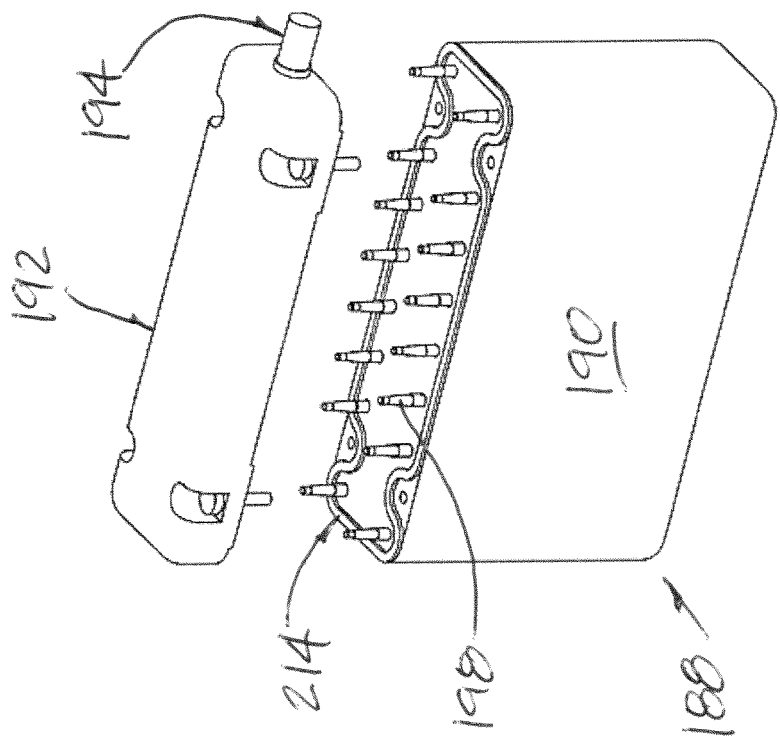

FIGS. 5 and 5A show the implantable device 188 illustrated in FIGS. 3 to 3E with two possible gasket seal designs. The gasket seal 214 of FIG. 5 and the gasket seal 216 of FIG. 5A both seal body fluids from leaking through the gap or seam located between the header 192 and the can housing 190. The gasket seal 214 depicted in FIG. 5 comprises a sealing band surrounding the array of connectors, such as the bodies 198. The gasket seal 216 depicted in FIG. 5A comprises a sealing layer with an opening at each body location to permit the bodies 198 to project therethrough. The seal 216 with sealing layer design has the further benefit of temporarily fixing the seal 216 from moving due to the bodies 198 projecting through the various openings on the sealing layer, which permits installation of the header 192 over the can housing 190 without the seal shifting.

FIG. 6 shows a partial side exploded view of an IMD 216 in accordance with another aspect of the present disclosure, which comprises a header 192, a can housing 190, and a lead cable 194 positioned inside a bore of the header 192. FIG. 6A shows the IMD 216 of FIG. 6 in perspective view. FIG. 6B also shows the IMD of FIG. 6 in a different perspective view. The IMD 216 is similar to IMD 188 illustrated in FIGS. 3 to 3E but wherein the bodies 198 are attached to the header while the contact housings 200 are attached to the can housing 190.

FIG. 7 shows a partial side exploded view of an IMD 218 in accordance with another aspect of the present disclosure, which comprises a header 192, a can housing 190, and a lead cable 194 positioned inside a bore of the header 192. FIG. 7A shows the IMD 218 of FIG. 7 in perspective view. FIG. 7B also shows the IMD of FIG. 7 in a different perspective view. The IMD 218 is similar to IMD 188 illustrated in FIGS. 3 to 3E but wherein some connectors have their bodies 198 attached to the can housing 190 and the rest have their bodies 198 attached to the header 192. Similarly, some contact housings 200 of the connectors are attached to the can housing 190 and the rest attached to the header 192.

FIG. 8 shows a partial side exploded view of an IMD 220 in accordance with another aspect of the present disclosure, which comprises a header 192, a can housing 190, and a lead cable 194 positioned inside a bore of the header 192. FIG. 8A shows the IMD 220 of FIG. 8 in perspective view. FIG. 8B also shows the IMD of FIG. 8 in a different perspective view. The IMD 220 of FIG. 8 is similar to the IMD 188 illustrated in FIGS. 3 to 3E but wherein the length of some of the bodies 198 of one set of connectors is different than the length of the bodies 198a of the rest of connectors. In other words, the bodies 198, 198a, which can comprise several elongated rods or shafts, have at least two different lengths, which are configured to be inserted into at least two different bores provided by contact housings 200, 200a. The relative lengths and relative bores of the bodies and of the contact housings are understood to be aligned or matched on the header 192 and the can housing 190 to enable latching between the corresponding set of connectors. In another embodiment, the bodies 198, 198a have different lengths while the bores of the various contact housings 200 have the same length, as further discussed below with reference to FIGS. 8C and 8D.

FIG. 8C presents a cross section of the implantable device 220 shown in FIGS. 8-8B in a partially assembled configuration, which shows the bodies 198, 198a inserted into the bores of the contact housings 200 but not fully inserted. FIG. 8D is a zoomed view of section S1 of FIG. 8C. A gap 222 is shown between the bottom surface 224 of the header 192 and the top surface 226 of the can housing 190, representing a partial installation. In the present view, the longer length body 198a contacts the inner spring 128 while the shorter length body 198 has not.

FIG. 8E shows the same cross section of the implantable device shown in FIG. 8C but in a fully assembled configuration. FIG. 8F is a zoomed view of section S2 of FIG. 8E. FIGS. 8C to 8F demonstrate how using connectors with different body lengths can lower the insertion force provided by the array. For example, the connectors with longer bodies 198a are those to first develop their break out force (FIGS. 8C and 8D), whereas the rest of the connectors (with shorter bodies 198) develop their break out force afterwards, which results in a lowered insertion force of the array. In other words, the final force to close the header 192 onto the can housing 190 has been reduced by configuring some of the elongated bodies 198a to contact the inner springs 128 located inside the contact housings 200 before the others so that not all contacts to the inner springs 128 occur simultaneously at the very last moment, which reduces the insertion force to assemble the header onto the can housing.

FIG. 9 shows a partial side exploded view of an IMD 228 in accordance with another aspect of the present disclosure, which comprises a header 192, a can housing 190, and a lead cable 194 positioned inside a bore of the header 192. FIG. 9A shows the IMD 228 of FIG. 9 in perspective view. FIG. 9B also shows the IMD of FIG. 9 in a different perspective view. The IMD 228 of FIG. 8 is similar to the IMD 188 illustrated in FIGS. 3 to 3E but wherein, in one set of connectors, one of the grooves or grooves of the contact housings 200 receiving one of the two or three electrically conductive canted coil springs, or a two-groove contact housing as shown in FIG. 1 or a three-groove contact housing as shown in FIG. 1C, respectively, is defined by a groove on the outer surface of one of the electrical terminals of the bodies 198 and a groove on the inner surface of the bore, which results in such set of connectors having the ability to latch or lock. In other words, the connector of FIG. 1A or 2A may be used as one of the connectors in the IMD.

FIG. 9C is a schematic cross section of the implantable device 228 shown in FIGS. 9 to 9B in a fully assembled configuration. FIG. 9D is a zoomed view of FIG. 9C at section S3. FIG. 8E is a zoomed view of FIG. 9D at section S4. As shown more clearly in FIG. 9E, the contact housing 200 comprises a groove comprising a V-bottom 230 and the body 198 comprises a groove 232 and wherein a spring 234 is located between the two grooves in a latching application, which permits separation in a latching application, or locking in a locking application. By locking, it is understood to mean that the body cannot separate from the contact housing without destroying the spring 234.

FIG. 10 shows a partial side exploded view of an IMD 234 in accordance with another aspect of the present disclosure, which comprises a header 192, a can housing 190, and a lead cable 194 positioned inside a bore of the header 192. FIG. 10A shows the IMD 234 of FIG. 10 in perspective view. FIG. 10B also shows the IMD of FIG. 10 in a different perspective view. The IMD 234 of FIG. 10 is similar to the IMD 188 illustrated in FIGS. 3 to 3E but wherein the connectors located at the corners of the array have been replaced by mechanical connectors 236, which also latch or lock but do not transmit electrical signals or currents.

Figure 10E:
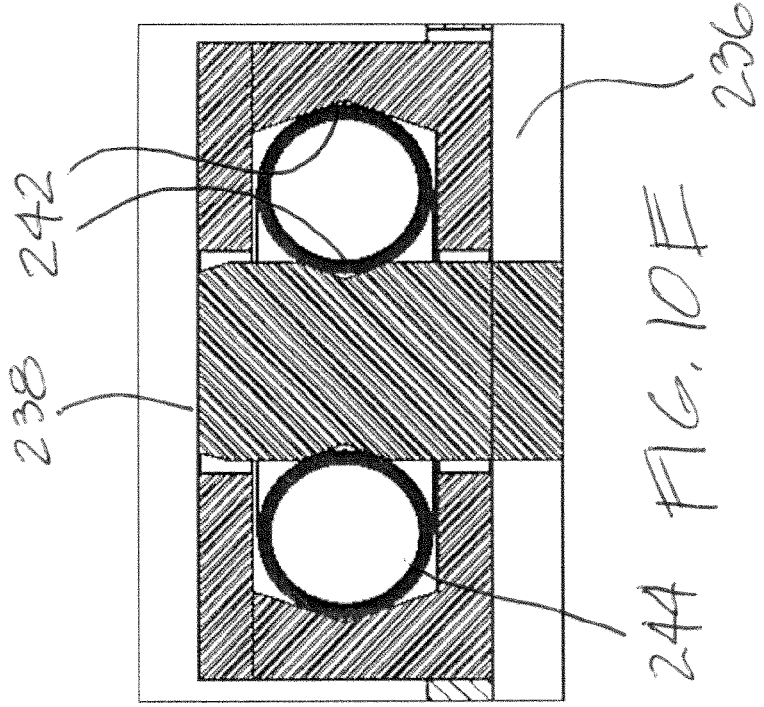
FIGS. 10 to 10E show an implantable device, which is similar to that illustrated in FIGS. 3 to 3E, wherein one or more of the connectors located at the corners of the array have been replaced by mechanical connectors, which can optionally not include any electrical flow capability.
Figure 10D:
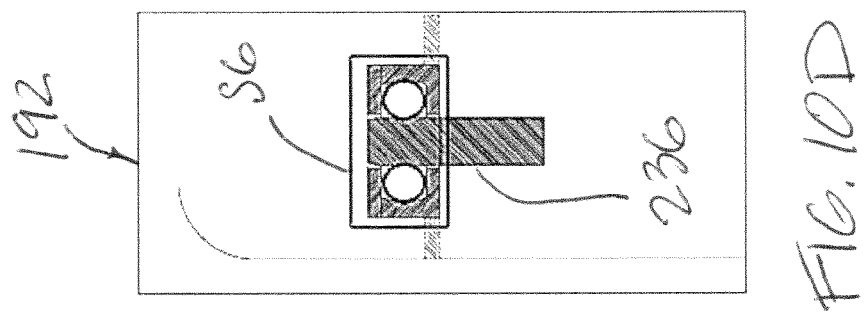
Figure 10C:
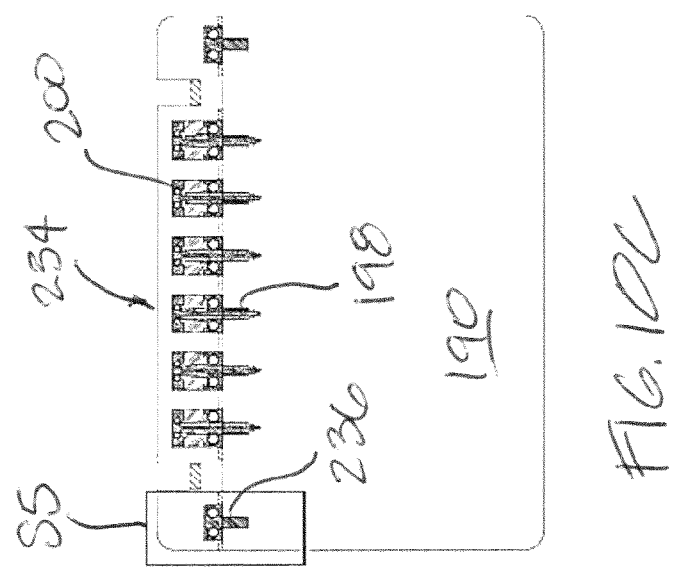

FIG. 10C is a cross section of the implantable device 234 shown in FIGS. 10 to 10B in a fully assembled configuration. FIG. 10D is a zoomed view of FIG. 10C at section S5. FIG. 10E is a zoomed view of FIG. 10D at section S6. The various views depicted in FIGS. 10C-10E show the corner mechanical connectors 236 incorporated into the IMD 234 of FIGS. 10-10B. As clearly shown in FIG. 10E, the fastener 236 comprises a grooved housing 242 for capturing a spring 244 with the groove 242 on the pin 238, which may be made from a conductive or non-conductive material.

Figure 11:
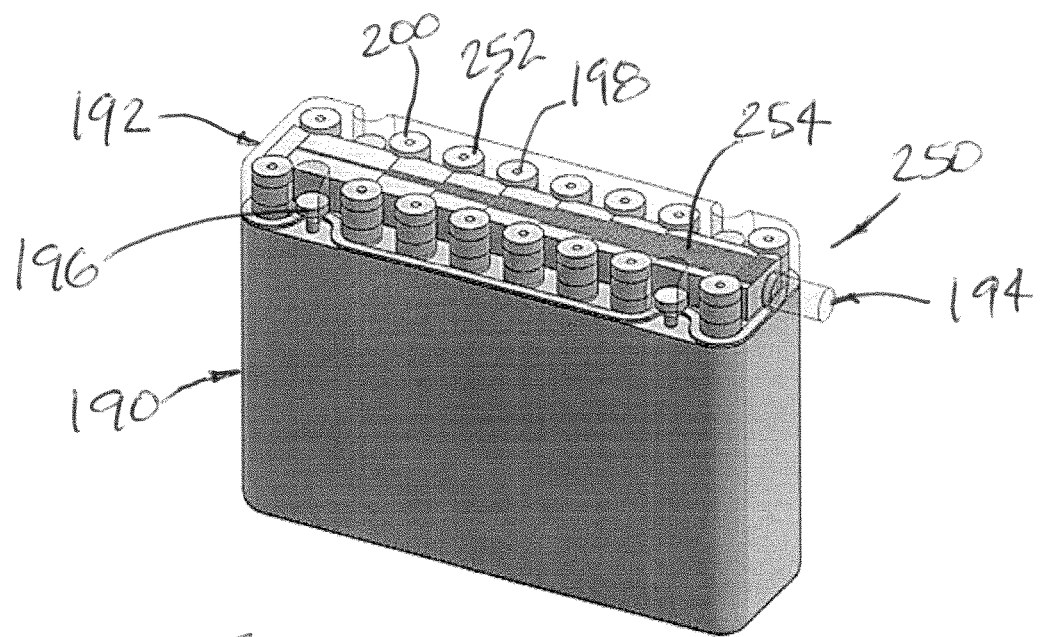
FIGS. 11 to 11C show an implantable device, which is similar to that illustrated in FIGS. 3 to 3E, wherein the header comprises a printed circuit board.

FIG. 11 shows a perspective view of an assembled IMD 250, similar to the IMD 188 illustrated in FIGS. 3 to 3E. The header 192 is shown semi-transparent to show the components positioned therein, which include the lead cable 194, a plurality of connectors 252, which comprise bodies 198 and contact housings 200, fasteners 196, and a printed circuit board (PCB), which defines the portion of the electrical paths going from the array of connectors 252 to the lead 194.

Figure 11A:
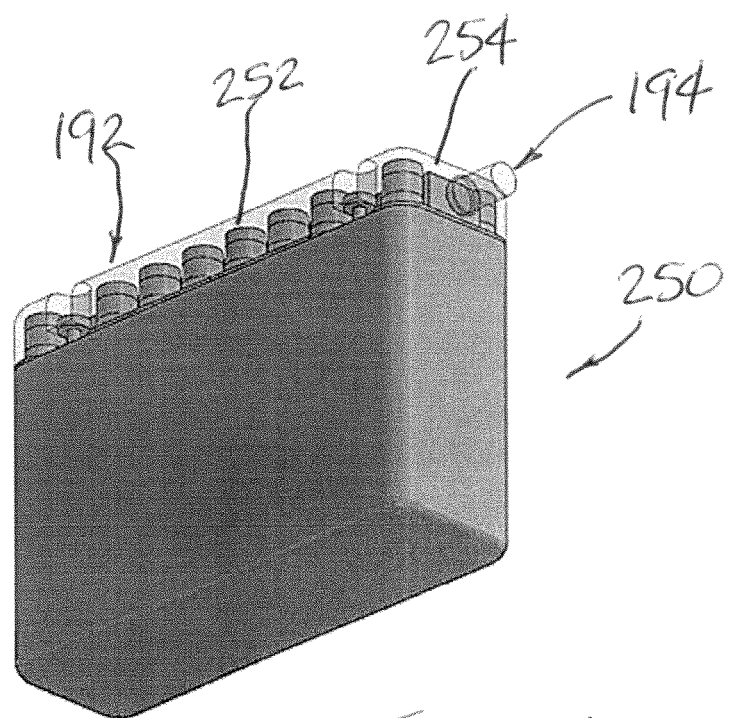

FIG. 11A shows the IMD 250 of FIG. 11 from a different perspective.

Figure 11B:
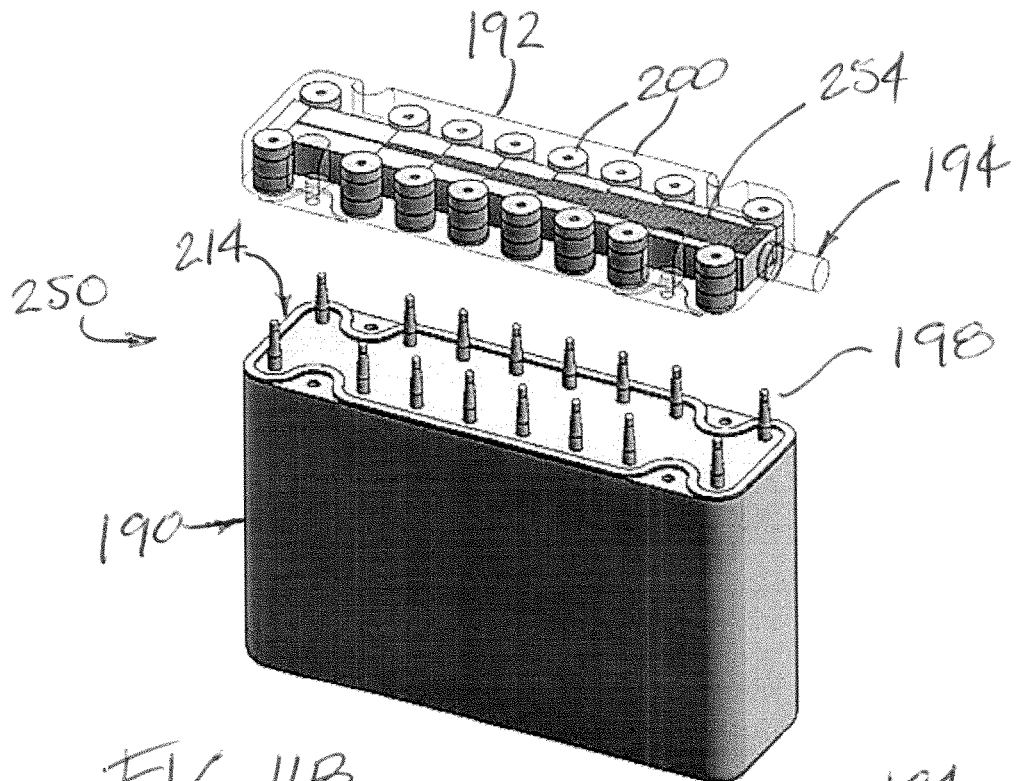

FIG. 11B shows the IMD 250 of FIG. 11 in a partially exploded state, which shows the header 192 having the housings 200, PCB 254 and lead cable 194 located therein and a plurality of bodies or pins 18 projecting from the can housing 190.

Figure 11C:
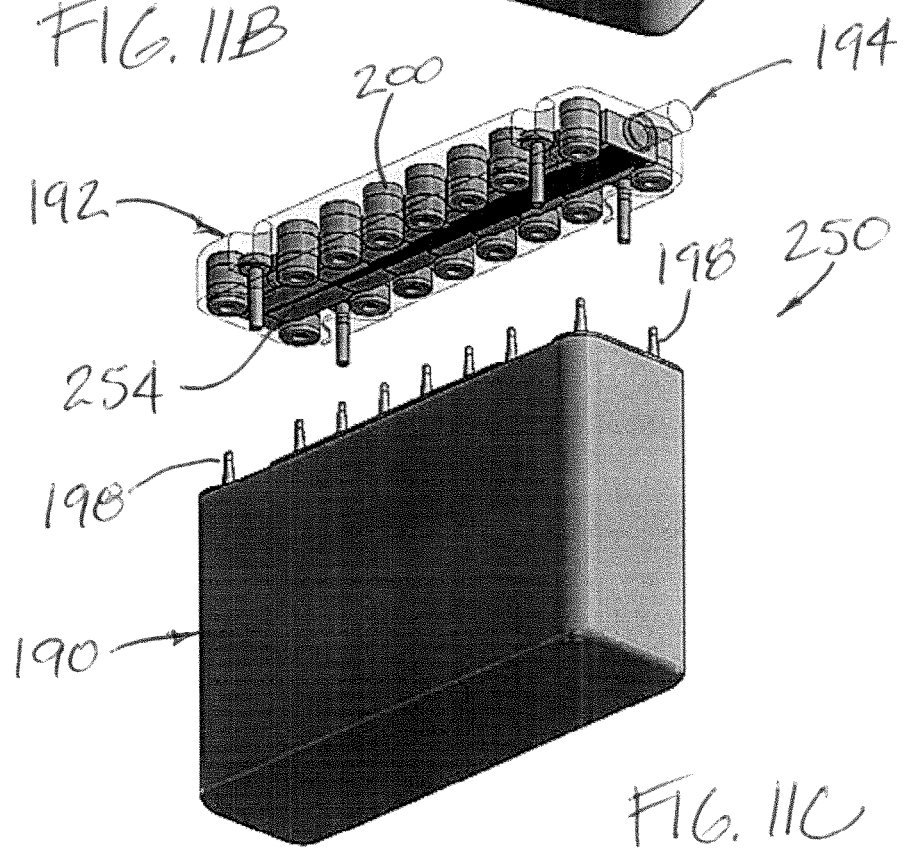

FIG. 11C shows the IMD 250 of FIG. 11B from a different perspective.

Figure 12:
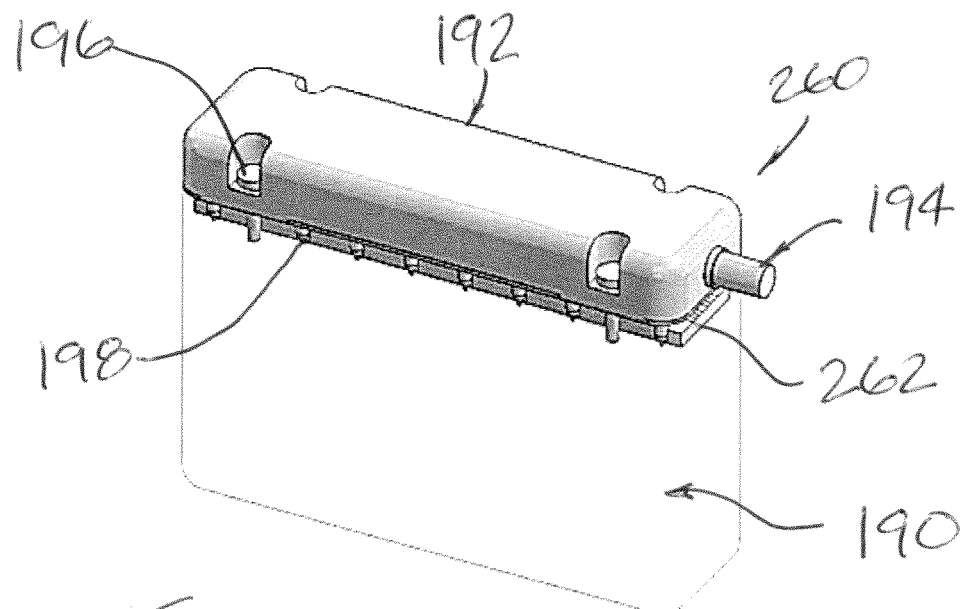
FIGS. 12 to 12C show an implantable device, which is similar to that illustrated in FIGS. 3 to 3E, wherein the can housing comprises a printed circuit board.

FIG. 12 shows a perspective view of an assembled IMD 260, similar to the IMD 188 illustrated in FIGS. 3 to 3E. The can housing 190 is shown semi-transparent to show some of the components positioned therein, which include a printed circuit board 262 that defines the portion of the electrical paths or traces 264 going from the electronics inside the can housing to the array of bodies 198 of the connectors.

Figure 12A:
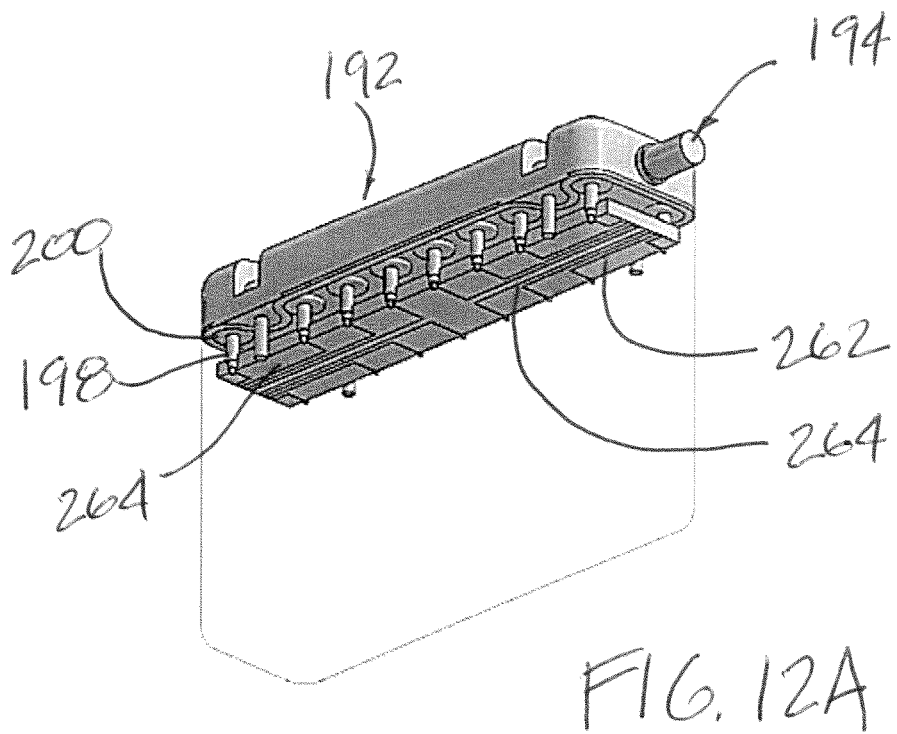

FIG. 12A shows the IMD 260 of FIG. 12 from a different perspective.

Figure 12B:
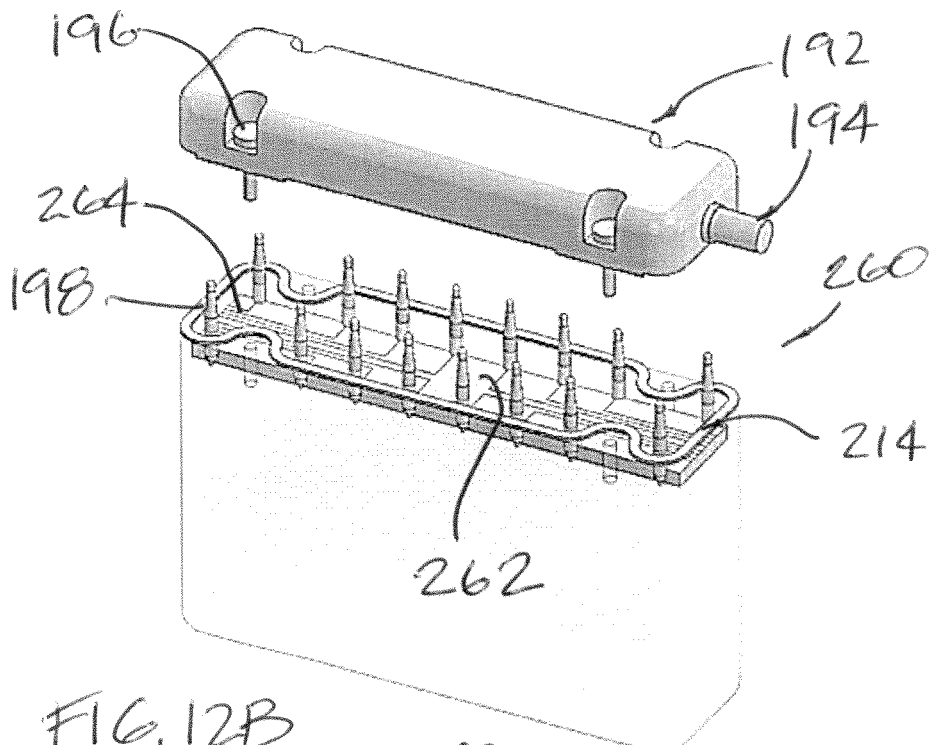

FIG. 12B shows the IMD 260 of FIG. 12 in a partially exploded state, which shows the can housing 190 having the bodies 198, PCB 262, traces 264, and gasket 214.

Figure 12C:
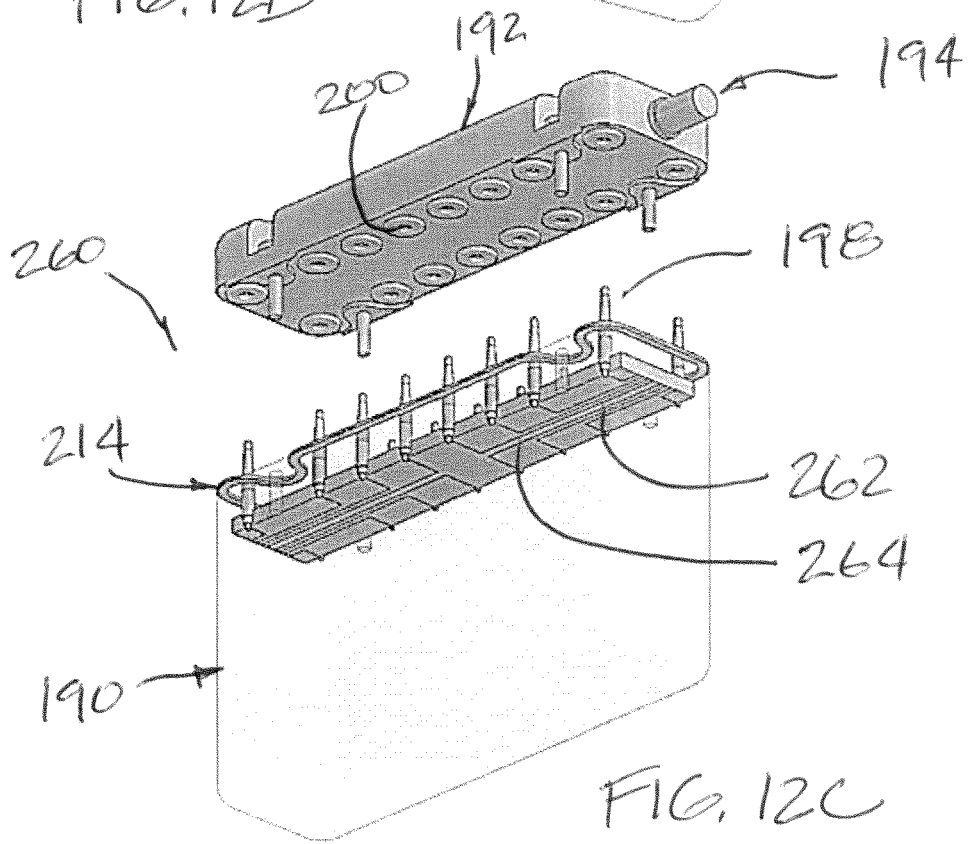

FIG. 12C shows the IMD 260 of FIG. 12 in a partially exploded state, in a different perspective, similar to FIG. 12B.

Figure 13:
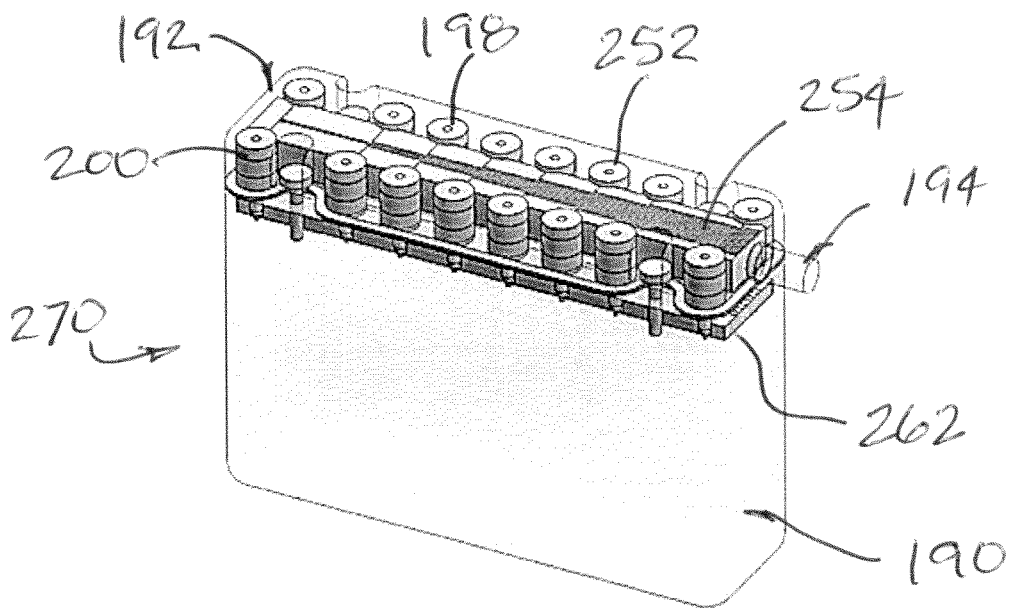
FIGS. 13 to 13C show an implantable device, which is similar to that illustrated in FIGS. 3 to 3E, wherein both the header and the can housing comprise a printed circuit board.

FIG. 13 shows a perspective view of an assembled IMD 270, similar to the IMD 188 illustrated in FIGS. 3 to 3E. Both the can housing 190 and the header are shown semi-transparent to show some of the components positioned therein. In the present embodiment, a PCB 254 is located in the header 192 and another PCB 262 in the can housing 190, the former defining the portion of the electrical paths going from the array of connectors to the lead and the latter defining the portion of the electrical paths going from the electronics inside the can housing to the array. The IMD is shown with the contact housings 200 being positioned in the header and the bodies 198, such as pins or shafts, positioned in or on the can housing 190. However, as discussed elsewhere herein, the arrangement can be reversed or the header and the can housing can have both components in a mixed arrangement.

Figure 13A:
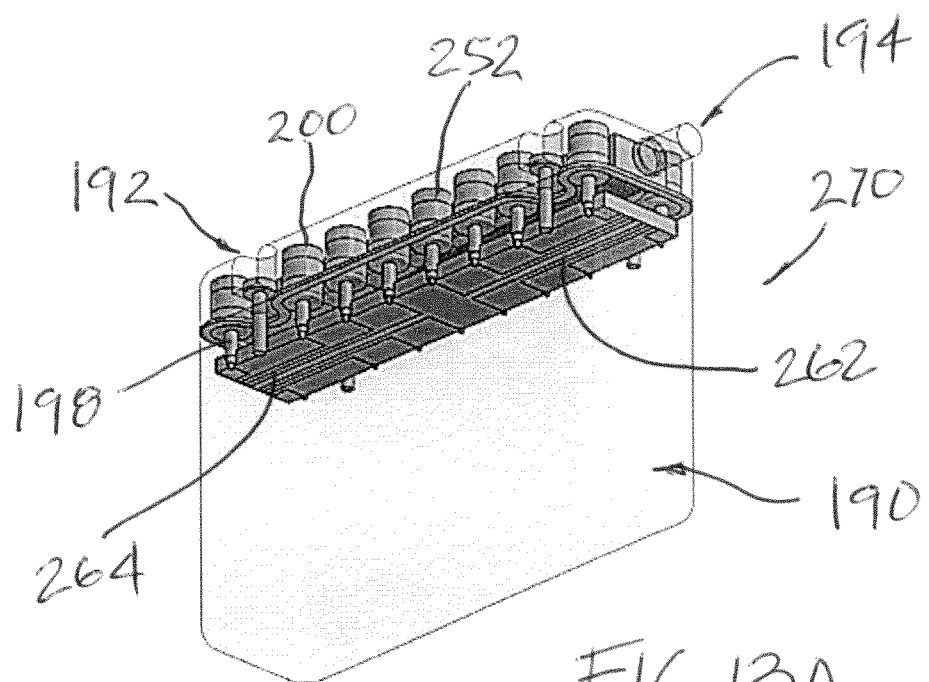

FIG. 13A shows the IMD 270 of FIG. 13 from a different perspective.

Figure 13B:
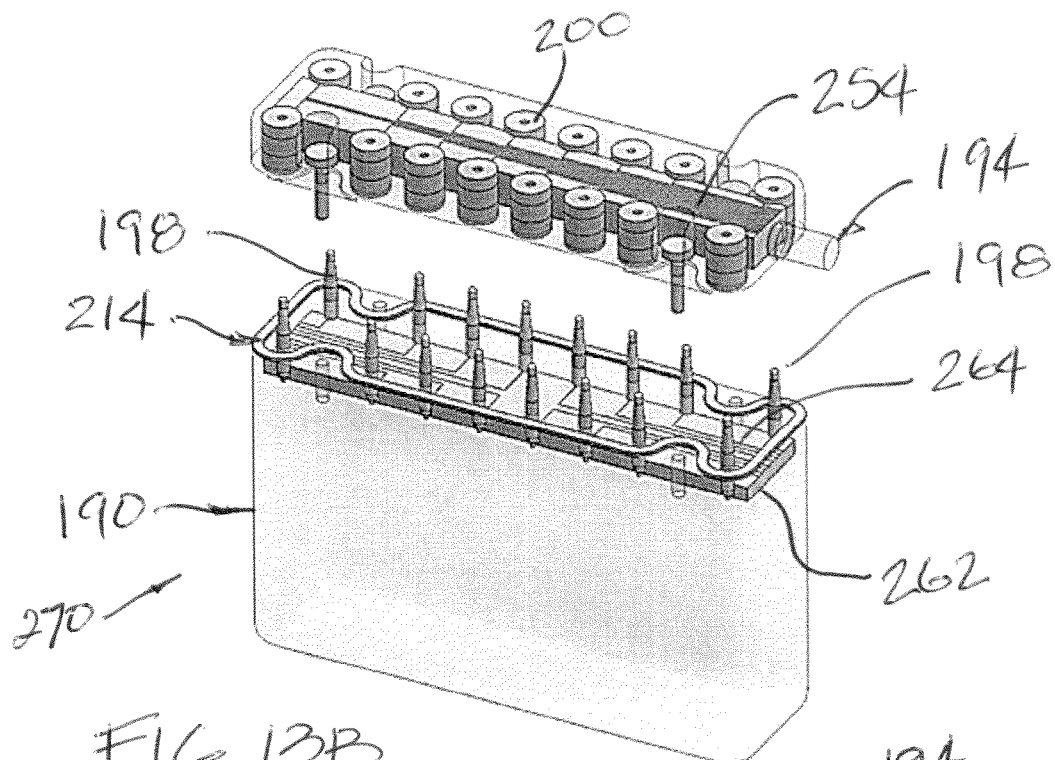

FIG. 13B shows the IMD 270 of FIG. 13 in a partially exploded state, which shows the can housing 190 having the bodies 198, PCB 262, traces 264, and gasket 214. FIG. 13B also shows the header comprising another PCB 254, the plurality of contact housings 200, and the lead cable 194.

Figure 13C:
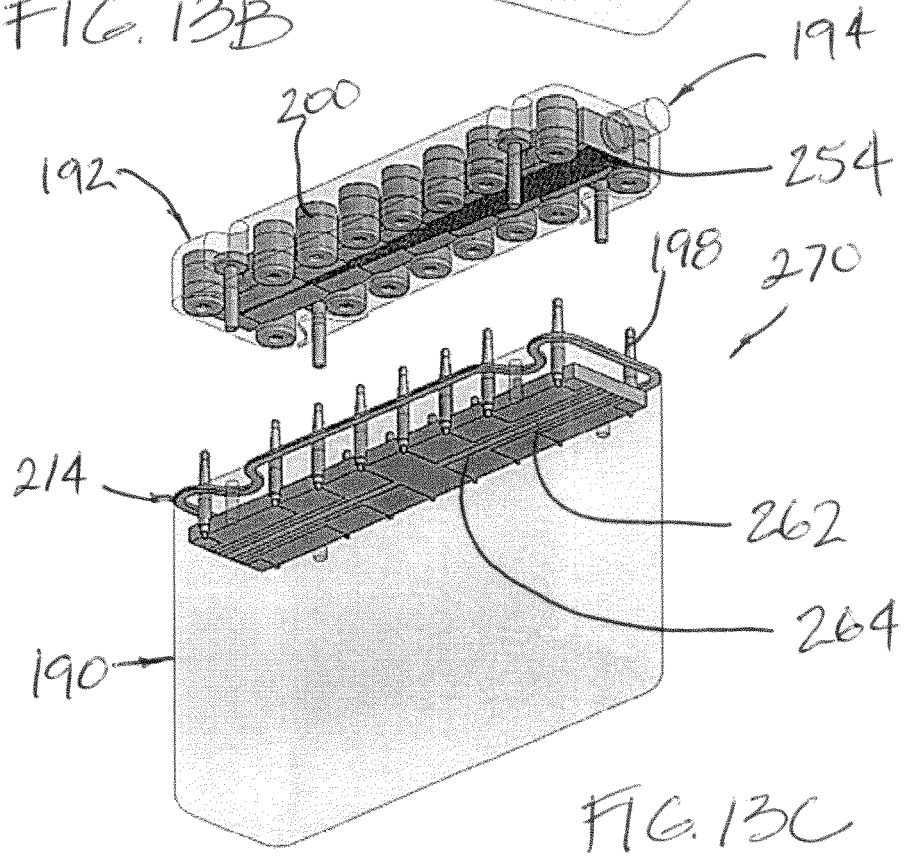

FIG. 13C shows the IMD 270 of FIG. 13 in a partially exploded state, in a different perspective, similar to FIG. 13B.

The printed circuit boards (PCBs) presented in FIGS. 11 to 13C can comprise two layers of printed circuits. Other configurations may also be possible.

Although limited embodiments of the connectors with electrical or signal carrying capabilities and their components have been specifically described and illustrated herein, many modifications and variations will be apparent to those skilled in the art. For example, the contact housing and the body, which can be an insertable member for inserting into a bore of the contact housing, can be attached to first and second structures that are other than expressly disclosed to provide electrical communication between the first and second structures. Furthermore, it is understood and contemplated that features specifically discussed for one connector or array of connectors may be adopted for inclusion with another connector or connector array embodiment, provided the functions are compatible. For example, mixed body and contact housing arrangement for an array on a single structure discussed for one connector or array embodiment may be used in another embodiment not described with both a body and a contact housing. Accordingly, it is to be understood that the connectors with electrical or signal carrying capabilities and their components constructed according to principles of the disclosed device, system, and method may be embodied other than as specifically described herein. The disclosure is also defined in the following claims.

The invention claimed is:

1. A connector comprising:
   a first housing comprising a first electrically conductive housing section, a second electrically conductive housing section and a housing sealing component at least partially isolating said first and second electrically conductive housing sections from each other; said first and second electrically conductive housing sections and housing sealing component having an outside diameter dimension and a bore;
   a body insertable into said bore, said body comprising a first electrical terminal and a second electrical terminal;
   a first electrically conductive spring positioned in a first groove defined at least in part by the first electrically conductive housing section and a second electrically conductive spring positioned in a second groove defined at least in part by the second electrically conductive housing section;
   a second housing comprising a bore having the first housing disposed therein, wherein an opening of said bore of said second housing is larger than the outside diameter dimension of the first housing; and
   said first electrically conductive housing section, said first electrically conductive spring and said first electrical terminal defining at least a portion of a first electrical path, and said second electrically conductive housing section, said second electrically conductive spring, and said second electrical terminal defining at least a portion of a second electrical path.

2. The connector of claim 1, wherein at least one of the first and second grooves is defined by a first groove on the inner surface of the bore and a second groove on the outer surface of the corresponding electrical terminal.

3. The connector of claim 1, further comprising a non-conductive layer separating the first electrical terminal from the second electrical terminal on the body.

4. The connector of one of claim 1, wherein at least a portion the bore and a portion of the body are tapered.

5. The connector of claim 1, wherein a portion of the bore between the first and the second electrically conductive springs and a portion of the body are tapered.

6. The connector of claim 1, wherein the housing sealing component is mechanically engaged to a second sealing component to at least partially isolate the first and second electrical terminals from each other.

7. The connector of claim 6, wherein the mechanical engagement of the housing sealing component and second sealing component is a latch or a detent.

8. The connector of claim 1, wherein at least one of the first and second electrically conductive springs is a canted coil spring.

9. The connector of claim 1, wherein at least one of the first and second electrically conductive springs is one of a garter spring and a ribbon spring.

10. The connector of claim 1, wherein at least one of the first and second electrically conductive springs is a finger spring.

11. The connector of claim 1, wherein the first housing is positioned in a planar structure; and wherein a third housing is positioned in the planar structure and spaced from the first housing.

12. The connector of claim 1, further comprising a first structure secured to a second structure by the connector.

13. The connector of claim 1, wherein the body is attached to a header or a can housing of an implantable medical device and the first housing is attached to the other one of the header or the can housing.

14. The connector of claim 13, further comprising a gasket seal located between the header and the can housing.

15. The connector of claim 14, wherein the gasket seal comprises an opening at a location of the body or the combination first and second electrically conductive housing sections and the housing sealing component.

16. The connector of claim 13, wherein a printed circuit board is located in the header and defines a portion of the first and second electrical paths.

17. The connector of claim 13, wherein the printed circuit board comprises two layers of printed circuits.

18. The connector of claim 1, wherein the body is attached to a first structure and the first housing is attached to a second structure to put the first structure in electrical communication with the second structure.

19. The connector of claim 18, wherein the first and the second structures are part of a land vehicle.

20. The connector of claim 18, wherein the first and the second structures are part of a flying aircraft.

21. The connector of claim 18, wherein the first and the second structures are part of a watercraft.

22. The connector of claim 18, wherein the first and the second structures are part of a consumer electronic device.

23. An array of connectors spaced from one another, each connector comprising:
   a first housing comprising a first electrically conductive housing, a second electrically conductive housing, and a housing sealing component at least partially isolating said first and second electrically conductive housings from each other; said first and second electrically conductive housings and said housing sealing component defining a bore with two seams defined by the first electrically conductive housing section and the housing sealing component and the second electrically conductive housing section and the housing sealing component;
   a body insertable into said bore comprising a first electrical terminal and a second electrical terminal;
   a first electrically conductive spring in a first groove defined at least in part by the first electrically conductive housing section and the housing sealing component and a second electrically conductive spring in a second groove defined at least in part by the second electrically conductive housing section and the housing sealing component;
   a second housing comprising a bore receiving the first housing therein, said second housing comprising a seam that is parallel to at least one of the two seams of the first housing; and
   said first electrically conductive housing section, said first electrically conductive spring, and said first electrical terminal defining at least a portion of a first electrical path, and said second electrically conductive housing section, said second electrically conductive spring, and said second electrical terminal defining at least a portion of a second electrical path.

24. The array of connectors of claim 23, wherein at least one groove in one of the connectors is aligned with a groove on an outer surface of a corresponding electrical terminal to capture a corresponding electrically conductive spring therebetween.

25. The array of connectors of claim 23, wherein, at least in one of the connectors, at least a portion of the bore is tapered.

26. The array of connectors of claim 23, wherein, at least in one of the connectors, a portion of the bore between two consecutive electrically conductive springs is tapered.

27. The array of connectors of claim 23, wherein, at least in one of the connectors, the housing sealing component is mechanically engaged to a second sealing component to at least partially isolate the first and second electrical terminals from each other.

28. The connector of claim 27, wherein the mechanical engagement of the housing and second sealing components is a latch.

29. The array of connectors of claim 23, wherein a length of the body of one of the connectors is different than a length of the body of another one of the connectors.

30. The array of connectors of claim 23, further comprising at least one mechanical connector positioned with the array of connectors.

31. The array of connectors of claim 23, wherein at least one of the first and second electrically conductive springs of at least one of the connectors is a canted coil spring.

32. The array of connectors of claim 23, wherein at least one of the first and second electrically conductive springs of at least one of the connectors is one of a garter spring and a ribbon spring.

33. The array of connectors of claim 23, wherein at least one of the first and second electrically conductive springs of at least one of the connectors is a finger spring.

34. A method for forming a connector comprising:
forming a first housing comprising by placing a housing sealing component in between a first electrically conductive housing section and a second electrically conductive housing section to at least partially isolate the first and second electrically conductive housing sections from each other; said first and second electrically conductive housing sections and said housing sealing component having an outside diameter dimension and a common bore;
assembling a first electrical terminal and a second electrical terminal together to form an insertable body;
placing a first electrically conductive spring in a first groove defined at least in part by the first electrically conductive housing section;
placing a second electrically conductive spring in a second groove defined at least in part by the second electrically conductive housing section;
forming a second housing comprising a bore having the first housing disposed therein, wherein an opening of said bore of said second housing is larger than the outside diameter dimension of the first housing; and
placing the insertable body into the bore of the first housing to form a first electrical path defined by the first electrically conductive housing section, the first electrically conductive spring, and the first electrical terminal and a second electrical path defined by the second electrically conductive housing section, the second electrically conductive spring, and the second electrical terminal.

35. The method of claim 34, further comprising placing a non-conductive layer between the first electrical terminal and the second electrical terminal to isolate the first and second electrical terminals from one another.

36. The method of claim 34, further comprising placing the first housing adjacent two or more first housings to form an array.

37. The method of claim 34, further comprising placing the insertable body adjacent two or more insertable bodies to form an array.

38. The method of claim 34, further comprising attaching the first housing to a first structure and attaching the insertable body to a second structure.

39. The method of claim 38, wherein the first structure and the second structure is part of a flying aircraft, a land vehicle, a watercraft, a medical device, a consumer electronic device, a wind turbine, or a satellite.

40. The method of claim 38, further comprising connecting the first housing and the insertable body.

* * * * *

UNITED STATES PATENT AND TRADEMARK OFFICE
CERTIFICATE OF CORRECTION

| | | |
|---|---|---|
| PATENT NO. | : 9,011,169 B2 | Page 1 of 1 |
| APPLICATION NO. | : 13/848678 | |
| DATED | : April 21, 2015 | |
| INVENTOR(S) | : Mark Russell et al. | |

It is certified that error appears in the above-identified patent and that said Letters Patent is hereby corrected as shown below:

On the Title page, in column 2, in "Primary Examiner", line 1, delete "Abullah Riyami" and insert -- Abdullah Riyami --, therefor.

In The Specification

In column 7, line 11, delete "8f" and insert -- 8F --, therefor.

In column 7, line 15, delete "9e" and insert -- 9E --, therefor.

In column 11, line 51, delete "bore" and insert -- bore. --, therefor.

In The Claims

In column 17, line 53, in claim 4, after "of" delete "one of".

In column 17, line 54, in claim 4, after "portion" insert -- of --.

Signed and Sealed this
Seventeenth Day of May, 2016

Michelle K. Lee
*Director of the United States Patent and Trademark Office*